US010851404B2

(12) United States Patent
Jiang et al.

(10) Patent No.: US 10,851,404 B2
(45) Date of Patent: Dec. 1, 2020

(54) LUCIFERIN-CONTAINING SUBSTRATE AND MONITORING DEVICE INCLUDING THE SUBSTRATE

(71) Applicant: 3M INNOVATIVE PROPERTIES COMPANY, St. Paul, MN (US)

(72) Inventors: Hongying Jiang, Woodbury, MN (US); Masayuki Nakamura, Woodbury, MN (US); Xuan Jiang, Maplewood, MN (US); Catherine A. Bothof, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/533,688

(22) PCT Filed: Dec. 4, 2015

(86) PCT No.: PCT/US2015/063939

§ 371 (c)(1),
(2) Date: Jun. 7, 2017

(87) PCT Pub. No.: WO2016/099950

PCT Pub. Date: Jun. 23, 2016

(65) Prior Publication Data

US 2017/0335368 A1 Nov. 23, 2017

Related U.S. Application Data

(60) Provisional application No. 62/093,042, filed on Dec. 17, 2014.

(51) Int. Cl.

| | |
|---|---|
| ***C07D 277/68*** | (2006.01) |
| ***C07D 417/04*** | (2006.01) |
| ***C12Q 1/66*** | (2006.01) |
| ***B01L 3/00*** | (2006.01) |

(52) U.S. Cl.

CPC .............. *C12Q 1/66* (2013.01); *B01L 3/5029* (2013.01); *C07D 277/68* (2013.01); *C07D 417/04* (2013.01); *C12Y 113/12007* (2013.01); *B01L 2300/046* (2013.01); *B01L 2300/047* (2013.01); *B01L 2300/0832* (2013.01); *B01L 2400/0481* (2013.01); *B01L 2400/0683* (2013.01); *G01N 2333/90241* (2013.01)

(58) Field of Classification Search

CPC ............................ C07D 277/68; C07D 417/04

See application file for complete search history.

(56) References Cited

U.S. PATENT DOCUMENTS

| | | | |
|---|---|---|---|
| 3,423,209 A | 1/1969 | Weber | |
| 4,668,558 A | 5/1987 | Barber | |
| 4,726,989 A | 2/1988 | Mrozinski | |
| 4,978,504 A | 12/1990 | Nason | |
| 5,069,403 A | 12/1991 | Marentic | |
| 5,133,516 A | 7/1992 | Marentic | |
| 5,158,557 A | 10/1992 | Noreen | |
| 5,175,030 A | 12/1992 | Lu | |
| 5,238,623 A | 8/1993 | Mrozinski | |
| 5,266,266 A | 11/1993 | Nason | |
| 5,514,120 A | 5/1996 | Johnston | |
| 5,691,846 A | 11/1997 | Benson, Jr. | |
| 5,783,148 A * | 7/1998 | Cottingham ........ | B01L 3/50273 422/417 |
| 5,783,399 A | 7/1998 | Childs | |
| 5,858,693 A | 1/1999 | Cottingham | |
| 5,876,995 A | 3/1999 | Bryan | |
| 5,879,635 A | 3/1999 | Nason | |
| 5,993,954 A | 11/1999 | Radovanovic | |
| 6,060,261 A | 5/2000 | Ryufuku | |
| 6,632,850 B2 | 10/2003 | Hughes | |
| 2002/0187076 A1 | 12/2002 | DiCesare | |
| 2008/0095856 A1 | 4/2008 | Jacobson | |
| 2011/0097723 A1 | 4/2011 | Liu | |

(Continued)

FOREIGN PATENT DOCUMENTS

| | | |
|---|---|---|
| WO | WO 1993-00994 | 1/1993 |
| WO | WO 1998-037299 | 8/1998 |

(Continued)

OTHER PUBLICATIONS

Mohler. Tips on Buying and Working with Luciferin. downloaded from www.genengnews.com/magazine/128/tips-on-buying-and-working-with-luciferin/. p. 1-5 (Year: 2010).*
Luciferin and Caged Luciferin. Invitrogen. p. 1-2 (Year: 2006).*
International Search report for PCT International Application No. PCT/US2015/063939 dated Mar. 17, 2016, 5 pages.

* cited by examiner

*Primary Examiner* — Taeyoon Kim
(74) *Attorney, Agent, or Firm* — Adrian L. Pishko

(57) ABSTRACT

Luciferin-containing substrates are provided including a substrate and luciferin dried on the substrate. The luciferin-containing substrate is free of a detectable amount of reactive luciferase. The substrate is optionally a nonwoven substrate. Monitoring devices are also provided. The monitoring devices include a test element having a test portion, a detection reagent comprising luciferase, a luciferin-containing substrate, and a container having a first end with an opening and a second end opposite the first end. The container is configured to receive the test portion and configured to be operationally coupled to an analytical instrument. The detection reagent and the luciferin each are capable of participating in one or more chemical reaction that results in the formation of a detectable product.

8 Claims, 5 Drawing Sheets

(56) References Cited

U.S. PATENT DOCUMENTS

| | | | | |
|---|---|---|---|---|
| 2011/0256531 | A1* | 10/2011 | Rajagopal | C12Q 1/66 435/6.1 |
| 2012/0082977 | A1* | 4/2012 | Rajagopal | C12M 23/32 435/6.1 |
| 2014/0099233 | A1 | 4/2014 | Bommarito | |

FOREIGN PATENT DOCUMENTS

| | | |
|---|---|---|
| WO | WO 2009-134509 | 11/2009 |
| WO | WO 2012-078426 | 6/2012 |
| WO | WO 2014-008150 | 1/2014 |
| WO | WO 2014-058652 | 4/2014 |
| WO | WO 2015-164632 | 10/2015 |

LUCIFERIN-CONTAINING SUBSTRATE AND MONITORING DEVICE INCLUDING THE SUBSTRATE

CROSS REFERENCE TO RELATED APPLICATIONS

This application is a national stage filing under 35 U.S.C. 371 of PCT/US2015/063939, filed Dec. 4, 2015, which claims the benefit of U.S. Application No. 62/093,042, filed Dec. 17, 2014, the disclosure of which is incorporated by reference in its/their entirety herein.

FIELD

The disclosure relates to using luciferin and luciferase for luminescent reactions, and to monitoring devices including luciferin and luciferase as detection agents.

BACKGROUND

Sampling programs are used to monitor critical raw materials, in-process materials, finished goods, and processing environments in the food and beverage industry. Routine sampling and testing can allow quality assurance personnel to detect undesirable materials, such as microorganisms, at a very early stage and take steps to prevent subsequent contamination of equipment and/or products. A variety of tests can be performed to detect the unwanted materials. Examples of such tests include chemical residue tests (e.g., Adenosine triphosphate (ATP) bioluminescence tests and protein colorimetric tests), culture methods, genetic tests (e.g., PCR), immunodiagnostic tests, and bioluminescent tests.

Sample-collection devices typically are used to collect surface samples for environmental tests. Commercially-available sample-collection devices include absorbent devices such as sponges, swabs, and the like. In addition, certain sample-collection devices are capable of collecting a predetermined volume of a liquid sample.

ATP is used routinely to detect a presence or absence of microorganisms in a sample. The chemical energy produced from the breakdown of ATP is converted into light energy. Each molecule of ATP consumed in the reaction produces one photon of light. A method for detecting ATP involves the luciferase/luciferin bioluminescent reaction. ATP is detected using an enzymatic reaction that involves the reaction of ATP with luciferase enzyme in the presence of luciferin and magnesium ion. This reaction results in the production of measurable light. This light output can be quantified in a luminometer. The presence of ATP in a sample may be a direct indicator of the presence of a microorganism (i.e., the ATP is derived from a microorganism) or the ATP may be an indirect indicator of the presence of a microorganism (i.e., the ATP is derived from vegetative or animal matter and indicates that nutrients that support the growth of microorganisms may be present in the sample). In addition, the presence or absence of ATP in a sample is used routinely to assess the efficacy of cleaning processes in food, beverage, other industrial processed, healthcare (e.g. endoscopes) and for such as cooling and process waters and/or to determine whether biocide treatment has been effective in reducing the level of microorganisms.

In some of these applications, refrigeration is not convenient and room temperature storage is preferred. The use of the luciferase/luciferin bioluminescent assay in some applications has been limited due to inadequate room temperature stability.

SUMMARY

Stabilized luciferin for luminescent reactions, and monitoring devices including luciferin for luminescent detection are provided. In a first aspect, luciferin-containing substrates are provided. More particularly, luciferin-containing substrates are provided including a substrate and luciferin dried on the substrate. The luciferin-containing substrate is free of a detectable amount of reactive luciferase.

In a second aspect, monitoring devices are provided. The monitoring devices include a test element having a test portion, a detection reagent comprising luciferase, a luciferin-containing substrate, and a container having a first end with an opening and a second end opposite the first end. The container is configured to receive the test portion and configured to be operationally coupled to an analytical instrument. The detection reagent, and the luciferin each are capable of participating in one or more chemical reactions that result in the formation of a detectable product.

In a third aspect, a method of making a luciferin-containing substrate is provided. The method includes applying to a substrate a solution containing luciferin and a solvent; and removing at least a portion of the solvent to dry the luciferin on the substrate. The luciferin-containing substrate is free of a detectable amount of reactive luciferase.

The substrates and monitoring devices provide improved luciferin stability and thus shelf life.

Figure 1:
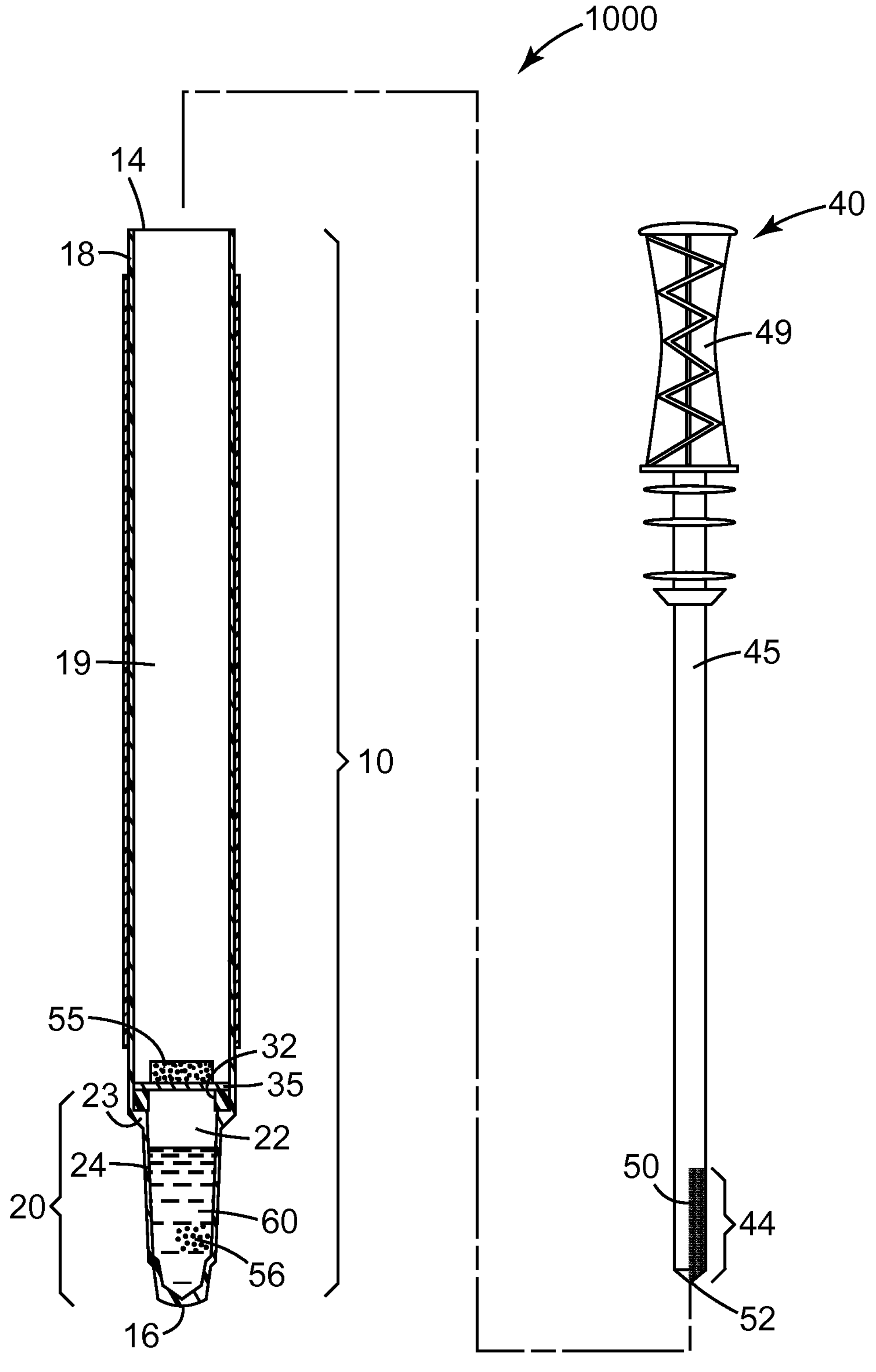
FIG. 1 is an exploded view of one embodiment of a monitoring device comprising a unitary container, shown in cross-section, and a test element according to the present disclosure.

While the above-identified drawings, which may not be drawn to scale, set forth various embodiments of the present disclosure, other embodiments are also contemplated, as noted in the detailed description.

DETAILED DESCRIPTION

Stabilized luciferin for luminescent reactions, and monitoring devices including luciferin for luminescent detection are provided.

In a bioluminescent reaction, luciferin contained as a luminescent substrate is apt to lose stability in the solution during storage. Conventional luminescent reagents containing luciferin can exhibit deterioration of the luminescent activity due to various degradation pathways of the luciferin and/or the enzyme luciferase. It has been found that luciferin can be stabilized by drying a luciferin-containing solution on a substrate and using the dried luciferin in a luminescent reaction. This inhibits degradation of enzymatically catalyzed luminescent activity at room temperature or higher and extends the product shelf life.

The recitation of any numerical range by endpoints is meant to include the endpoints of the range, all numbers within the range, and any narrower range within the stated range (e.g. 1 to 5 includes 1, 1.5, 2, 2.75, 3, 3.8, 4, and 5). Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "a", "an", and "the" are used interchangeably with "at least one" to mean one or more of the elements being described.

The term "and/or" means either or both. For example, the expression "A and/or B" means A, B, or a combination of A and B.

"Degradation" refers to loss of enzymatic activity of a reactive system including luciferin, luciferase, and adenosine triphosphate (ATP), with aging of at least one of the reactive system components when stored in the dark, as compared to the enzymatic activity of a control system. The control system is the same reactive system, in which all of the components were stored in the dark at a temperature of 4° C. or lower.

"Foam" refers to a material having pockets of gas trapped in a solid.

"Hydrophobic" refers to a material that exhibits a water contact angle of 90° or larger on its surface.

"Hydrophilic" refers to a material that exhibits a water contact angle of less than 90° on its surface.

Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

Stabilized luciferin for luminescent reactions, and monitoring devices including luciferin for luminescent detection are provided. In a first aspect, luciferin-containing substrates are provided. More particularly, luciferin-containing substrates are provided including a substrate and luciferin dried on the substrate. The luciferin-containing substrate is free of a detectable amount of reactive luciferase. The phrase "luciferin dried on the substrate" as used herein refers to luciferin affixed to a substrate in a dried state. The term "dried" with respect to a luciferin-containing substrate refers to a moisture content of the luciferin-containing substrate of up to 5 percent by weight of water, or up to 4 percent by weight of water, or up to 3 percent by weight of water, or up to 2 percent by weight of water. The luciferin is attached to the substrate as a result of contacting the substrate with a solution or suspension containing luciferin and removing the solvent, such as via evaporation, freeze-drying, or filtering. "Luciferin dried on the substrate" is in contrast to dry luciferin that is placed on a substrate (e.g., luciferin powder disposed on a piece of filter paper, a polymeric film, etc.). For porous substrates, a portion of the luciferin is typically located within the thickness of the substrate as opposed to dried primarily on one or more major surfaces of the substrate.

In a second aspect, monitoring devices are provided. The monitoring devices include a test element having a test portion, a detection reagent comprising luciferase, a luciferin-containing substrate, and a container having a first end with an opening and a second end opposite the first end. The container is configured to receive the test portion and configured to be operationally coupled to an analytical instrument. The detection reagent and the luciferin each are capable of participating in one or more chemical reactions that result in the formation of a detectable product.

The below embodiments relate to both the first aspect and the second aspect.

The substrate is not particularly limited. For instance, the substrate is optionally selected from a nonwoven substrate, a woven substrate, a foam substrate, a polymeric film substrate, a membrane substrate, a metal foil substrate, and a microreplicated film substrate. In certain embodiments, the substrate is a nonwoven substrate. Considerations for selecting a suitable substrate include the efficiency of removal of the luciferin from the substrate when contacted with a fluid (e.g., a solvent, a detection reagent, etc.) and the capability of the substrate material to minimize degradation of the luciferin dried on the substrate. Regarding the efficiency of removal of the luciferin from the substrate, in some cases a porous substrate enhances the contact between the dried luciferin and the fluid, thereby increasing the detachment of the luciferin from the substrate. The luciferin has sufficient affinity for the material of the substrate that it can attach to the substrate upon drying, yet the luciferin also has sufficient affinity for the fluid that it readily dissolves/disperses into the fluid rather than remaining disposed on the substrate (e.g., remaining absorbed into the fibers, the foam, the sheet, or other structure of the substrate material). It has been discovered that both hydrophobic and hydrophilic substrates can be suitable for the luciferin-containing substrate. Moreover, in certain embodiments the substrate comprises at least two polymeric materials, although in some cases one of the two or more polymeric materials alone would not provide a suitable substrate. The substrate optionally comprises cellulose, viscose, rayon, polyethylene terephthalate (PET), nylon, cotton, aluminum foil, polycarbonate (PC), polyvinylidene fluoride (PVDF), polyether sulfone (PES), polypropylene (PP), polylactic acid (PLA), polyvinyl alcohol (PVA), or a combination thereof.

In certain embodiments, the substrate comprises a nonwoven substrate. A nonwoven substrate is often in the form of a layer of interlaid fibers that are not woven or knitted together. Suitable nonwoven substrates can be prepared by any suitable process such as, for example, air laying techniques, spunlaid techniques such as meltblowing or spunbonding, carding, wetlaying, and combinations thereof. Fibers suitable for use in preparing a nonwoven substrate are usually pulpable or extrudable fibers such as those that are stable to radiation and/or to a variety of solvents. Useful fibers typically include polymeric fibers or cellulose fibers. In many embodiments, the fibers include polymeric fibers, such as one or a plurality of different types of polymeric fibers. For example, at least some of the polymeric fibers can be selected to exhibit a degree of hydrophilicity. In certain embodiments, the fibers include blown melt fibers. In other embodiments, the fibers include cellulose fibers, such as provided by paper and filter paper.

In certain embodiments, the substrate comprises a woven substrate. A woven substrate is often in the form of a layer of interlaid fibers that are knitted or woven together to form a fabric. Fibers suitable for use in preparing a woven substrate typically include natural or synthetic fibers such as rayon, cotton, nylon, viscose, polyester, or a combination thereof.

In certain embodiments, the substrate comprises a foam substrate, for example and without limitation, a polymeric foam comprising a polyolefin, a polyurethane, a poly(meth) acrylate, or neoprene. Synthetic foams are particularly well suited because the foam is a flexible, compliant material that can absorb liquid. Synthetic foams are typically less hydrophilic and have a low ability to retain liquid within the structure as compared to natural foams, such as a cellulose sponge. Therefore, although fluid is easily absorbed in the material, the fluid is also easily removed from the less hydrophilic foam, which could be useful in detaching the luciferin. In many embodiments, the porous elastomeric material comprises an open cell foam.

In certain embodiments, the substrate comprises a polymeric film substrate. In certain embodiments, a polymeric film substrate has a thickness between about 1 mil (25.4 micrometers) and about 10 mils (254 micrometers), and can be made via extrusion or casting techniques known to the skilled practitioner. Suitable polymeric materials for the polymeric films include for example and without limitation, polyethylene terephthalate (PET), nylon, polycarbonate (PC), polyvinylidene fluoride (PVDF), polyether sulfone (PES), polypropylene (PP), polylactic acid (PLA), and polyvinyl alcohol (PVA). One suitable polymeric film is a 7 mil-thick (175 micrometers) PC film commercially available under trade designation LEXAN from GE Advanced Materials (Pittsfield, Mass.).

In certain embodiments, the substrate comprises a membrane substrate. In certain embodiments, the membranes for use in aspects of the present disclosure include Thermally Induced Phase Separation (TIPS) membranes. The pore size of TIPS membranes can be generally controlled due to the ability to select the extent of stretching of the membrane material. TIPS membranes are relatively inexpensive to make, and methods for making them are known to the skilled practitioner. For example, various membranes and methods are described in detail in U.S. Pat. No. 4,726,989 (Mrozinski), U.S. Pat. No. 5,238,623 (Mrozinski), U.S. Pat. No. 5,993,954 (Radovanovic et al.), and U.S. Pat. No. 6,632,850 (Hughes et al.). Membranes for use in aspects of the present disclosure also include Solvent Induced Phase Separated (SIPS) membranes and other membranes made by extrusion, extrusion/stretching and extrusion/stretching/extraction processes, and track etching processes. Suitable membranes that may be formed by SIPS include for example and without limitation polyvinylidene fluoride (PVDF), polyether sulfone (PES), polysulfone (PS), polyacrylonitrile (PAN), nylon (i.e., polyamide), cellulose acetate, cellulose nitrate, regenerated cellulose, and polyimide. Suitable membranes that may be formed by track etching processes include for example and without limitation polycarbonate and polyester. Suitable membranes that may be formed by stretching techniques include for example and without limitation polytetrafluoroethylene (PTFE) and polypropylene.

In certain embodiments, the membrane substrate comprises a thermoplastic polymer, for instance polyethylene, polypropylene, 1-octene, styrene, polyolefin copolymer, polyamide (e.g., nylon), poly-1-butene, poly-4-methyl-1-pentene, polyethersulfone (PES), ethylene tetrafluoroethylene, polyvinylidene fluoride (PVDF), polysulfone, polyacrylonitrile, polyamide, cellulose acetate, cellulose nitrate, regenerated cellulose, polyvinyl chloride, polycarbonate, polyethylene terephthalate (PET), polyimide, polytetrafluoroethylene, ethylene chlorotrifluoroethylene, or combinations thereof. One suitable PVDF membrane is commercially available under trade designation 0.2 Micron GV from EMD Millipore (Billerica, Mass.).

In certain embodiments, the substrate comprises a metal foil substrate. A foil is a thin sheet of metal, such as aluminum, gold, tin, or copper. One suitable metal foil is commercially available under trade designation REYNOLDS Aluminum Foil from Reynolds Consumer Products LLC (Lake Forest, Ill.).

In certain embodiments, the substrate comprises a microreplicated substrate, such as a microreplicated film. "Microreplicated film" means a film having a topography in at least one major, substantially continuous surface that is essentially, but not necessarily perfectly, the inverse of the microembossed pattern to which the film surface is contacted. Polymers useful in forming a structured layer in articles of the invention include but are not limited to polyolefins such as polyethylene and polyethylene copolymers, polypropylene, ethylene/vinyl acetate polymers, ethylene/ethyl acrylate polymers. Other useful polymeric materials include vinyl polymers (e.g., polyvinyl chloride, polyvinyl alcohol, vinyl chloride/vinyl alcohol copolymers, polyvinylidene chloride, polyvinylidine diflouride (PVDF)), acrylate polymers (e.g., polymethyl methacrylate), polycarbonate polymers, polyesters (e.g., polyethylene terephthalate), polyamides (e.g., nylon), polyurethanes, polysaccharides (e.g. cellulose acetate), polystyrenes (e.g., polystyrene/methyl methacrylate copolymer), polysiloxane polymers (e.g., polysiloxane and organopolysiloxane polymers). The making of structured surfaces, and in particular microstructured surfaces, on a polymeric layer such as a polymeric film are disclosed in U.S. Pat. Nos. 5,069,403 and 5,133,516, both to Marentic et al. Structured layers may also be continuously microreplicated using the principles or steps described in U.S. Pat. No. 5,691,846 to Benson, Jr. et al. Other patents that describe microstructured surfaces include U.S. Pat. No. 5,514,120 to Johnston et al., U.S. Pat. No. 5,158,557 to Noreen et al., U.S. Pat. No. 5,175,030 to Lu et al., and U.S. Pat. No. 4,668,558 to Barber.

Methods for preparing luciferin-containing substrates are not particularly limited. For instance, in any embodiment a luciferin-containing substrate can be prepared by dissolving powdered luciferin into autoclaved deionized water to form a luciferin solution, then pipetting a volume of the luciferin solution onto a substrate. The luciferin-containing substrate is then allowed to dry, such as for about three or four hours at room temperature, or overnight in a lyophilizer. Preferably, once the luciferin solution is added to the substrate, exposure to light is minimized or prevented. Metal foil can be employed to cover the luciferin-containing substrate to protect it from light during drying, storage, etc.

In certain embodiments, the luciferin is present in the luciferin-containing substrate in an amount of at least 0.002 micrograms per substrate, or at least 0.005 micrograms per substrate, or at least 0.01 micrograms per substrate, or at least 0.05 micrograms per substrate, or at least 0.10 micrograms per substrate, or at least 0.15 micrograms per substrate, or at least 0.20 micrograms per substrate, or at least 0.30 micrograms per substrate, or up to 0.50 micrograms per substrate, or up to 0.25 micrograms per substrate; such as between 0.002 micrograms and 0.50 micrograms per substrate, or between 0.10 micrograms and 0.50 micrograms per substrate, or between 0.15 micrograms and 0.25 micrograms per substrate. The phrase "per substrate" refers to the piece of substrate, regardless of shape or size, on which the luciferin is deposited. In certain embodiments, the substrate is of a size that fits inside a monitoring device.

The amount of luciferin present in the luciferin-containing substrate is the amount of d-luciferin extractable from the substrate and measured by chiral high-pressure liquid chromatography (HPLC) to determine the fraction of total luciferin present as the active d-luciferin form. Accordingly, any 1-luciferin isomer present is not considered part of the amount of luciferin present. For example and without limitation, d-luciferin can be extracted from the luciferin-containing substrate with an aqueous buffer such as N-(2-acetamido)iminodiacetic acid (ADA). The d-luciferin extract can then be analyzed by chiral HPLC with fluorescence detection, for instance by injecting 25 microliter volumes of the extract onto a chiral column (e.g., a 100×4.6 mm Chiralpak AGP 5 μm column (Daicel Chiral Technologies Inc.)) using an eluent (e.g., of 92/8 (v/v) water/methanol for a 5 minute gradient followed by an eluent of 20/80 water/methanol for a 5 minute gradient and then holding for 10 minutes before re-equilibration with the 92/8 water/methanol eluent for an additional 5 minutes). Luciferin species are detected by fluorescence using excitation at 330 nm and emission at 522 nm. The resulting peak area of the d-luciferin peak is normalized to the sum of the peak areas of all luciferin related peaks is defined as the stable fraction of the d-luciferin.

The thickness of the substrate is not particularly limited as long as a fluid can penetrate the thickness of the substrate to remove the luciferin from the luciferin-containing substrate to participate in a luminescent reaction. For instance, in some embodiments the substrate comprises a thickness of 10 micrometers to 500 micrometers, or a thickness of 25 micrometers to 250 micrometers.

As noted above, the luciferin-containing substrate is free of a detectable amount of reactive luciferase. "Free of reactive luciferase" refers to the enzyme luciferase that is 1) present in an amount that is too low to generate a detectable luminescent signal when reacted with luciferin and ATP; 2) denatured or otherwise chemically unreactive; or 3) both 1) and 2). Stated another way, denatured, degraded, or generally unreactive luciferase that is not capable of reacting with luciferin and ATP to generate a detectable luminescent signal is not "reactive luciferase", regardless of the amount of luciferase present.

For applications in which the luciferin-containing substrate is used for determining the presence of adenosine-5'-triphosphate (ATP), the luciferin-containing substrate is free of any detectable amount of ATP to avoid generating false positive results.

To further decrease degradation of the luciferin, in many embodiments the luciferin-containing substrate is disposed in a package that blocks visible light, such as a package including metal foil, metal-coated plastic film, opaque plastic, or the like.

Advantageously, it has been discovered that luciferin-containing substrates according to various embodiments of the present disclosure exhibit decreased degradation as compared to luciferin in solution. As noted above, "degradation" refers to loss of enzymatic activity of a reactive system including luciferin, luciferase, and adenosine triphosphate (ATP), with aging of at least one of the reactive system components, as compared to a control system. In certain embodiments, less than 20% of an enzymatic activity is lost over a time of 10 weeks when the luciferin-containing substrate is stored at a temperature between 22° C. and 25° C. in the dark, or over a time of 4 weeks when stored at a temperature between 22° C. and 25° C. in the dark. In certain embodiments, less than 35% of an enzymatic activity is lost over a time of 10 weeks when the luciferin-containing substrate is stored at a temperature between 22° C. and 25° C. in the dark, or over a time of 8 weeks, or over a time of 4 weeks, when stored at a temperature between 22° C. and 25° C. in the dark. Similarly, when luciferin-containing substrates according to the present disclosure are exposed to temperatures higher than 25° C., such as during shipping or storage, less than 35% of an enzymatic activity is lost over a time of 4 weeks when the luciferin-containing substrate is stored at a temperature between 37° C. and 45° C. in the dark.

FIG. 1 shows an exploded view of one embodiment of a monitoring device 100 according to the present disclosure. The monitoring device 100 comprises a container 10 and a test element 40. The test element 40 comprises a test portion 44, to which a (optional) test composition 50 is releasably adhered, and a handle 49. The container 10 has a first end 12 and a second end 16 opposite the first end. The first end 12 of the container 10 comprises an opening 14 into which at least a portion of a test element 40 can be inserted.

The container 10 can be formed (e.g., by injection molding or extrusion) of polymeric materials (e.g., polyethylene, polypropylene) as a unitary part. As with the existing test devices described herein, when detection of an analyte comprises optical detection of a product derived therefrom, the container 10 should be formed using materials and processes that permit the transmission of wavelengths of light that are suitable to permit optical detection of the product.

Optionally, the monitoring device 100 further may comprise a frangible seal 35 disposed in the container 10. The frangible seal 35, if present, can partition the container 10 into two chambers: a receiving chamber 19 proximate the opening 14 and a cuvette chamber 22 distal the opening 14. The frangible seal 35 can be made from a water-resistant material such as, for example, a plastic film, a metal foil, or a metal-coated plastic film. The frangible seal 35 can be coupled to the container 10 via coupling means that are known in the art (e.g., an adhesive, an ultrasonic weld, and the like). The frangible seal 35 may be directly coupled (not shown) to the container 10 at a structure such as a flange 23, for example. Alternatively, the frangible seal 35 can be coupled (e.g., via an adhesive, an ultrasonic weld, or the like) to a separate structure (e.g., sealing member 32), which can be inserted into the container 10 and disposed against the flange 23, as shown in FIG. 1. The sealing member 32 can be formed from a relatively flexible and/or malleable material such as, for example, polyethylene, polypropylene, silicone, or butyl rubber. Preferably, the frangible seal 35 and sealing member 32, if present, form a liquid-resistant barrier between the receiving chamber 19 and the cuvette chamber 22.

The monitoring device further comprises a luciferin-containing substrate 55 disposed in the container. In the illustrated embodiment, the luciferin-containing substrate 55 is disposed in the container on the frangible seal 35. In some embodiments (see, e.g., FIG. 6), the monitoring device may comprise a second frangible seal 57 disposed between the first frangible seal 35 and the opening 14. The space between the first and second frangible seals forms a compartment in which the luciferin-containing substrate 55 can be disposed. The monitoring device further comprises a detection reagent 56 comprising luciferase disposed in the container. In the illustrated embodiment, the detection reagent 56 comprising luciferase is dissolved/suspended in a solvent as described below. In any embodiment, the detection reagent comprising luciferase is disposed in the container as a solid (e.g., a solid powder) separated from the luciferin-containing substrate to prevent premature interaction of the luciferin and the luciferase.

The container 10 can be formed (e.g., by injection molding or extrusion) of polymeric materials (e.g., polyethylene, polypropylene, polystyrene, polycarbonate). The walls of the cuvette portion 20 can be molded, for example, to form one of a variety of geometric shapes such as, for example, cubic, cuboid, cylindrical, conical, frusto-conical, other geometric shapes suitable to be operationally coupled to an analytical instrument (not shown). Preferably, the wall 24 of the cuvette portion 20 can be configured (e.g., by using a relatively transparent or translucent material and/or by constructing the cuvette portion with at least one relatively thin wall 24) to permit the transmission of light (e.g., visible light) into and/or out of the cuvette portion.

Accordingly, the monitoring device 100 includes an optional test composition 50, a test element 40 having a test portion 44 to which the optional test composition 50 is releasably adhered, a detection reagent 56, a luciferin-containing substrate 55, and a container 10 having a first end 12 with an opening 14 and a second end 16 opposite the first end 12. The container 10 is configured to receive the test portion 44 and configured to be operationally coupled to an analytical instrument 2500 (see, e.g., FIG. 8). The detection reagent and the luciferin each are capable of participating in one or more chemical reactions that result in the formation of a detectable product.

An optional lamina (not shown) can be affixed (e.g., adhesively affixed) to the container (e.g., proximate the opening). The lamina can be made from paper or a plastic film, for example, and may be used as a label.

Optionally, in any embodiment, the container can include a solvent disposed therein. In the illustrated embodiment, the first solvent 60 is disposed in the cuvette chamber 22. In any embodiment (not shown), the solvent alternatively or additionally may be disposed in the receiving chamber 19. In any embodiment, the frangible seal 35 can prevent unintended movement of the first solvent 60 between the receiving chamber 15 and the cuvette chamber 22.

In any embodiment, the first solvent 60 can be a liquid in which a portion or all of the optional test composition 50 is soluble. In any embodiment, the first solvent 60 may comprise water. In some embodiments, the first solvent 60 additionally comprises a buffer component to maintain the solvent within a predefined pH range (e.g., a pH range that is suitable for a reaction used in the detection of an analyte). In some embodiments, the solvent may comprise a surfactant (e.g., a nonionic surfactant) to facilitate the dispersion of the optional test composition 50 into the first solvent 60. A suitable surfactant does not substantially interfere with a reaction, luciferin, luciferase, and/or an instrument that is used for the detection of luminescence. In some embodiments, the solvent may comprise a stabilizer (e.g. enzyme stabilizers).

A monitoring device of the present disclosure comprises a detection reagent comprising luciferase for detecting the presence of ATP. At least one detection reagent may be disposed in the container. In any embodiment, at least one detection reagent may be disposed in a sealed chamber (e.g., the cuvette chamber) of the container. In any embodiment, the at least one detection reagent may be dissolved in the solvent. In some embodiments, (not shown) the detection reagent may be disposed on (e.g., as a coating such as a dried coating) and/or in the test element (e.g., dissolved in a solvent disposed in a reservoir, as disclosed herein). Suitable detection reagents to detect ATP include luciferin and luciferase. It has been discovered that upon aging luciferin and luciferase together, the reaction of luciferin with luciferase and ATP has less enzymatic activity (e.g., generates less luminescence) than if the luciferin and luciferase are aged separately. Surprisingly, the reaction of luciferin with luciferase and ATP has less enzymatic activity if just the luciferin is aged than if just the enzyme luciferase is aged. Accordingly, for the luciferin/luciferase/ATP reactive system, the "one or more chemical reaction that results in the formation of a detectable product" refers to the enzymatic activity of the reactive system.

Referring back to FIG. 1, the test element 40 comprises a test portion 44 and an optional stem 45. The stem 45 can be constructed from a variety of materials, such as wood, plastic, metal, or combinations thereof. In some embodiments, the stem 45 can be fabricated from a sufficiently flexible material (e.g., metal wire or plastic polymer) to insert the test portion 44 into tortuous spaces. In other embodiments, the stem 45 can be relatively inflexible. The stem 45 is adapted to be coupled (e.g., by friction fit or via an adhesive) to the handle 49. In use, the stem 45 or the handle 49 can be grasped by an operator in order to avoid contact between the operator and the test portion 44 and/or the optional test composition 50.

In any embodiment, the test portion 44 can be a substantially smooth surface such as, for example, a portion of the stem 45, as illustrated in FIG. 1. Alternatively, the test portion may include additional (e.g., 3-dimensional) structural features. In any embodiment, the test optional composition 50 can be applied as a liquid mixture and/or liquid suspension to the test portion 44 using processes that are known in the art including, for example, kiss coating, dip coating and spray coating. A portion or all of the liquid can subsequently be removed from the composition by evaporation (e.g., by placing the test element into a biosafety hood at ambient temperature (e.g., about 23° C.) for about 2-3 hours, for example). In the illustrated embodiment of FIG. 1, the test portion 44 is shown in partial section in order to show the optional test composition 50 coated on one side of the test portion and the underlying structure (e.g., the stem 45) on the other side of the test portion. In any embodiment, the optional test composition 50 may be coated on the entire circumference of the test portion.

Figure 2:
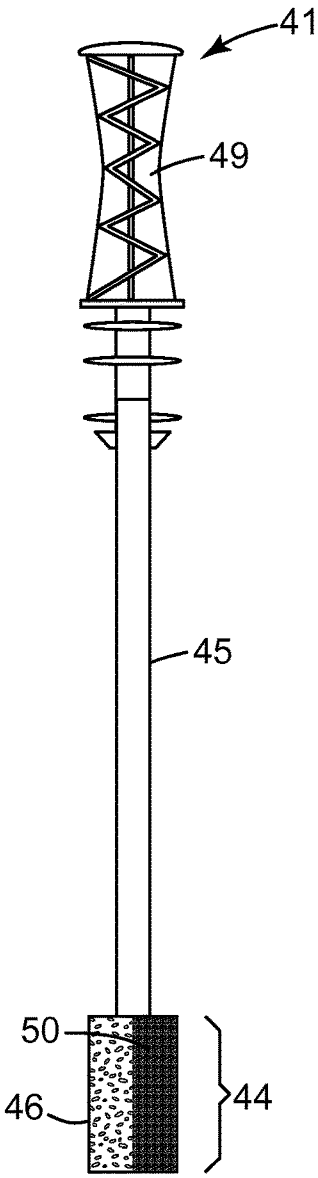
FIG. 2 is a side view of a test element, partially in section, having an alternative test portion comprising a foam material.

FIG. 2 shows one embodiment of a test element 41 having a test portion 44 with 3-dimensional structural features. The test element 41 can be used in any embodiment of the monitoring devices, methods, and systems of the present disclosure. The test portion 44 comprises a foam material 46 that is optionally imbued with the test composition 50. The foam material 46 comprises individual cells or void spaces in which and to which the optional test composition 50 can be releasably adhered. Suitable foam materials for use in a test portion 44 of the present disclosure should releasably retain the optional test composition 50 thereon. Non-limiting examples of suitable foam materials include polyurethane foams, polyethylene foams, and polystyrene foams. In some embodiments, the foams may be treated (e.g., corona-treated or electron beam-treated) in order to make the surface of the polymer more hydrophilic. The foam material 46 can be coupled to the stem 45, if present, or handle 49 using materials (e.g., melt bond, ultrasonic weld, adhesives, mechanical fasteners, or the like) and processes known in the art. In the illustrated embodiment of FIG. 2, the test portion 44 is shown in partial section in order to show the optional test composition 50 coated on one side of the test portion and the underlying structure (e.g., foam material 46) on the other side of the test portion. In any embodiment, the optional test composition 50 may be coated on the entire circumference of the test portion.

Figure 3:
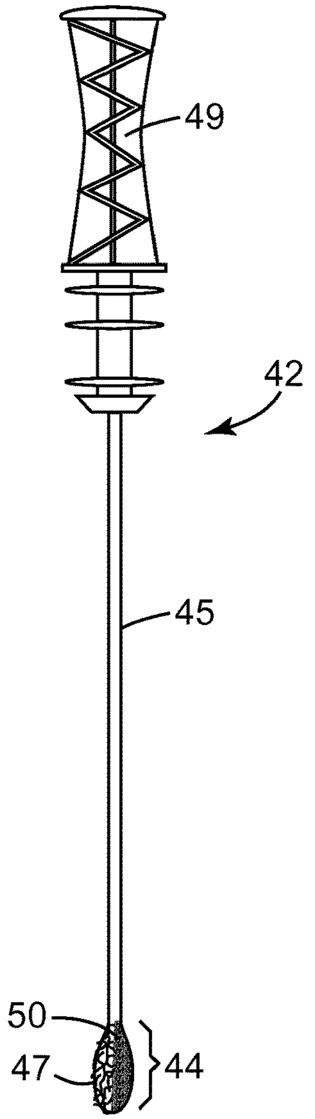
FIG. 3 is a side view of a test element, partially in section, having an alternative test portion comprising a fibrous material.

FIG. 3 shows an alternative embodiment of a test element 42 having a test portion 44 with 3-dimensional structural features. The test element 42 can be used in any embodiment of the monitoring devices, methods, and systems of the present disclosure. The test portion 44 comprises a fibrous material 47. The fibrous material 47 may comprise nonwoven fibers, as shown in FIG. 3, or woven fibers (not shown). The fibrous material comprises individual fibers with void spaces there between. The optional test composition can be releasably adhered to the surface of the fibers and, optionally, may fill void spaces between the fibers. Suitable fibrous materials for use in a test portion 44 of the present disclosure should releasably retain the optional test composition 50 thereon. Non-limiting examples of suitable fibrous materials include cotton, DACRON polyester, rayon, nylon, flocked nylon, polyester, polypropylene, and polyethylene. In some embodiments, the fibrous material may be treated (e.g., corona-treated, electron beam-treated, or coated with diamond-like glass) in order to make the surface of the material more hydrophilic. The fibrous material can be coupled to the stem 45, if present, or the handle 49 using materials (e.g., adhesives, mechanical fasteners, or the like) and processes (e.g., fiber entanglement) known in the art. In the illustrated embodiment of FIG. 3, the test portion 44 is shown in partial section in order to show the optional test composition 50 coated on one side of the test portion and the underlying structure (e.g., the fibrous material 47) on the other side of the test portion. In any embodiment, the optional test composition 50 may be coated on the entire circumference of the test portion.

Figure 4A:
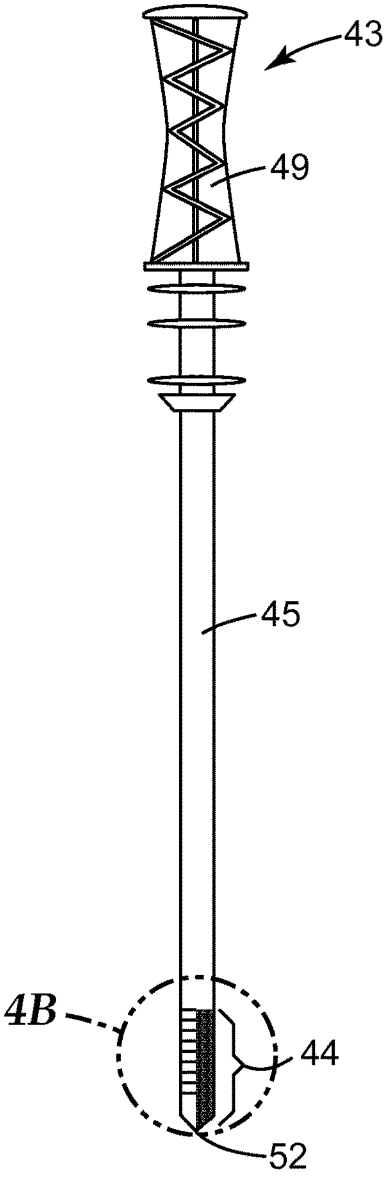
FIG. 4A is a side view of a test element, partially in section, having an alternative test portion comprising a plurality of recessed areas.
Figure 4B:
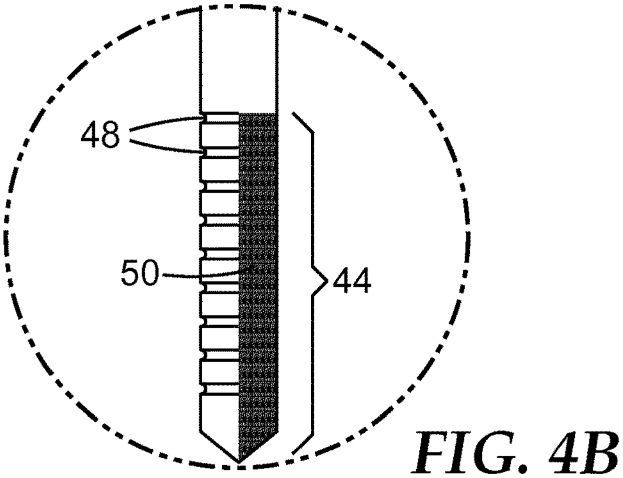
FIG. 4B is a detail view of the test portion of the test element of FIG. 4A.

FIG. 4 shows another alternative embodiment of a test element 43 having a test portion 44 with 3-dimensional structural features. The test element 43 can be used in any embodiment of the monitoring devices, methods, and systems of the present disclosure. The test portion 44 in this embodiment comprises one or more cavity 48. In this embodiment, the stem 45 and the test portion 44 may be formed as a unitary part or may be formed as separate parts that are coupled together (e.g., by friction fit or via an adhesive). The test portion 44 may be formed at least in part of relatively rigid polymer (e.g., nylon, polysulfone, polycarbonate, or combinations thereof) or it may be formed using a more compliant polymer, such as silicone. Suitable materials for the test portion 44 include, but are not limited to, any thermoplastic materials suitable for casting, profile extrusion, molding (e.g., injection molding) or embossing including, for example, polyolefins, polyesters, polyamides, poly(vinyl chloride), polymethyl methacrylate, polycarbonate, nylon, and the like. In other embodiments, the test portion 44 may be formed by molding or embossing a sheet of suitable material into the desired cavity structure. In some embodiments, the test portion 44 may be treated (e.g., corona-treated or electron beam-treated) in order to make the surface of the material more hydrophilic. In the illustrated embodiment of FIG. 4, the test portion 44 is shown in partial section in order to show the optional test composition 50 coated on one side of the test portion and the underlying structure (e.g., cavities 48) on the other side of the test portion. In any embodiment, the optional test composition 50 may be coated on the entire circumference of the test portion.

In any embodiment, the test portion can comprise a porous fibrous nonwoven matrix (not shown). In any embodiment, the nonwoven matrix can comprise a wet-laid fiber matrix fabricated from polyethylene fibers (e.g., 1 denier fibrillated polyethylene fibers), nylon fibers (e.g., 6 denier, 5.08-cm chopped nylon fibers), bicomponent polymeric fibers (e.g., 1 denier bicomponent ethylene vinyl acetate/polypropylene fibers), or glass fibers. In any embodiment, the optional test composition can be disposed on and/or in the fibrous nonwoven matrix. Processes for the production of suitable wet-laid fiber matrixes are described, for example in International Publication No. WO 2012/078426.

A person having ordinary skill in the art will recognize a variety of design configurations can be used for the one or more cavity in the test element 43. For example, International Publication No. WO 2009/134509 discloses a variety of sample acquisition devices comprising cavities that are suitable for use as in a test portion 44 of a test element 43. International Patent Publication No. WO 1993/00994 also discloses a sample acquisition device with a plurality of grooves capable of retaining a sample. One or more of the grooves described therein could be used in a test element according to the present disclosure.

In any embodiment, the test element may be configured to actuate (i.e., open) the frangible seal. Referring back to FIG. 4, the test element 43 comprises a piercing tip 52 that is shaped to puncture a frangible seal. Alternatively or additionally, the stem 45 of any test element can be formed from a material (e.g., wood, metal, plastic) that is rigid enough such that, when urged against a frangible seal, the stem can deform and/or rupture the frangible seal.

The optional test composition is releasably adhered to the test portion of the test element. The test composition is dispersible, and may be soluble, in an aqueous solvent.

In any embodiment, the optional test composition may be prepared as a homogeneous mixture in a suitable solvent (e.g., water and/or an alcohol). In any embodiment, the optional test composition may be dissolved or suspended in an organic solvent before it is applied to the test element. In any embodiment, the optional test composition can be applied as a single solution and/or suspension to the test portion of the test element (e.g., using processes described herein) in a single application. Alternatively, the optional test composition can be applied to the test portion of the test element as two or more separate solutions and/or suspensions. The first solution and/or suspension may be permitted to dry or partially dry before the second solution and/or suspension is applied.

Figures 5A, 5B, 5C:
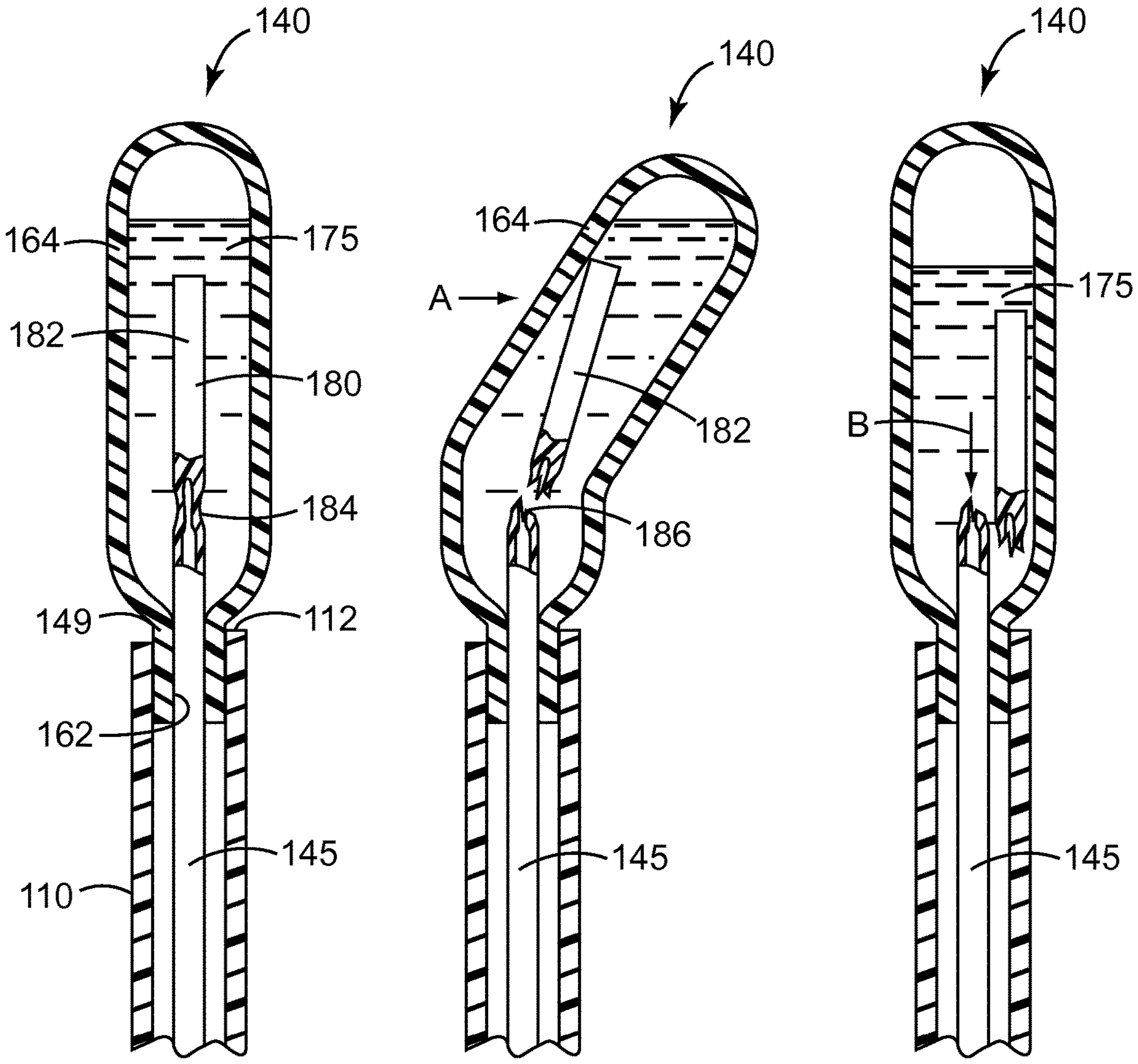
FIG. 5A-C are side views, partially in section, of a portion of one embodiment of an alternative test element comprising a hollow stem, a deformable reservoir, and a breakable valve that places the reservoir in selective fluid communication with the stem, showing how deformation of the reservoir causes breakage of the valve permitting the flow of a liquid into the stem.

In any embodiment, the monitoring device can comprise a test element that is adapted to deliver a liquid to the container. Nason (U.S. Pat. No. 5,266,266) discloses a specimen test unit that includes a swab member that can be adapted to function as a test element according to the present disclosure. FIGS. 5A-C show a portion (i.e., the portion proximate the first end 112 of the container 110) of one embodiment of a test element 140 that is adapted to deliver a second solvent 175 to the container 110. In this embodiment, the handle 149 comprises a hollow channel 162 extending there through. Coupled to the handle 149 (e.g., via an adhesive (not shown) or by friction fit) is a reservoir 164 with a hollow stem 145 coupled thereto (e.g. by friction-fit).

A portion 180 of the hollow stem 145 disposed in the reservoir 164 comprises a liquid flow regulator (e.g., a breakable liquid flow regulator) capable of placing the reservoir in fluid communication with the hollow stem 145. The portion 180 includes a solid rod segment 182 and a score 184 that facilitates the breakage of the stem 145, thereby creating a stem opening 186 to permit liquid flow through out of the reservoir through the hollow stem 145. The test element 140 can be made as described by Nason. As shown in FIG. 5B, (e.g., manual pressure) pressure against the flexible reservoir 164 in the direction of arrow "A" causes the reservoir 164 to deflect against the rod segment 182, causing the score 184 to fracture and optionally separate from the hollow stem 145 (as shown in FIG. 5C), which permits the flow of second solvent 175 through the stem opening 186 and into the hollow stem 145, as shown by arrow "B". A person having ordinary skill in the art will recognize other liquid flow regulator means (e.g., frangible ampoules and other means disclosed in U.S. Pat. Nos. 4,978,504 and 5,879,635) that can be used to place the second solvent 175 in the reservoir 164 into fluid communication with the hollow stem 145.

In any embodiment, the second solvent 175 can be a liquid in which a portion or all of the optional test composition (not shown) is soluble. In any embodiment, the second solvent 175 may comprise water. In some embodiments, the second solvent 175 additionally comprises a buffer component to maintain the solvent within a predefined pH range (e.g., a pH range that is suitable for a reaction used in the detection of an analyte). In some embodiments, the solvent may comprise a surfactant (e.g., a nonionic surfactant) to facilitate the dispersion of the optional test composition 50 into the second solvent 175. A suitable surfactant does not substantially interfere with a reaction, a detection reagent, and/or instrument that is used for the detection. In any embodiment the second solvent 175 may be the same as the first solvent (not shown), if present in the monitoring device.

Figure 6:
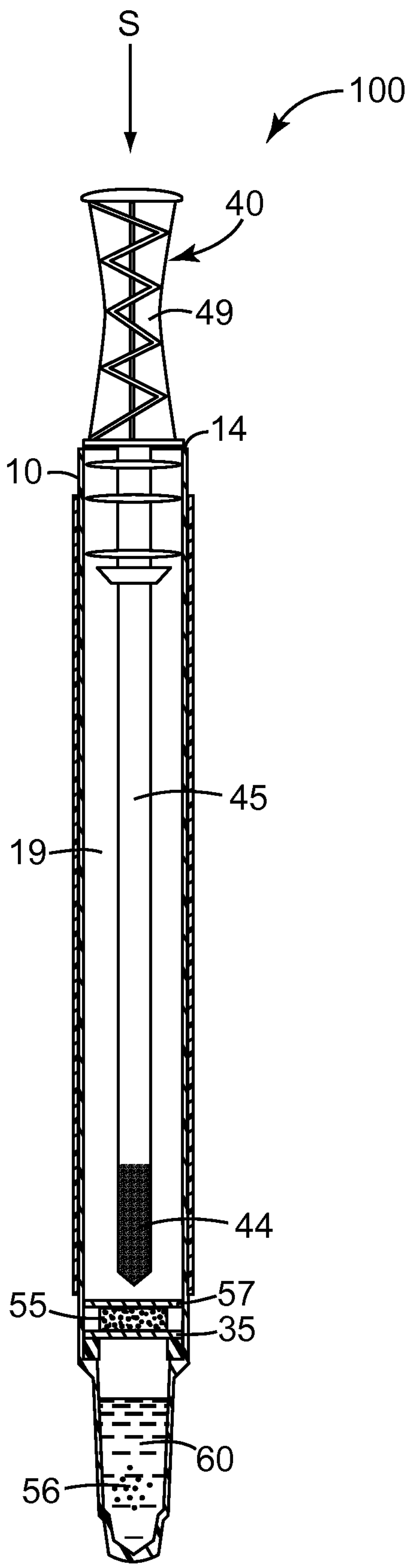
FIG. 6 is a side view, partially in section of the assembled monitoring device of FIG. 1 with the test element disposed in a first operational position with respect to the container.

FIG. 6 shows a side view, partially in section of one embodiment of a monitoring device 100 with the test element inserted into the container. In the illustrated embodiment, the test element 40 is disposed in a first operational position with respect to the container 10. In the first operational position, a first portion of the test element (e.g., the test portion 44 and stem 45) are disposed in the receiving chamber 19 of the container 10 and a second portion of the test element (e.g., the handle 49) is operationally coupled (e.g., by friction fit) with the container 10 proximate the opening 14 of the container. In the embodiment illustrated in FIG. 6, the luciferin-containing substrate 55 is encased between the frangible seal 35 and a second frangible seal 57. The second frangible seal 57, similar to the (first) frangible seal 35, can be made from a water-resistant material such as, for example, a plastic film, a metal foil, or a metal-coated plastic film, to protect the luciferin-containing substrate 55 from the atmosphere (or any other contents) of the receiving chamber 19.

Figure 7:
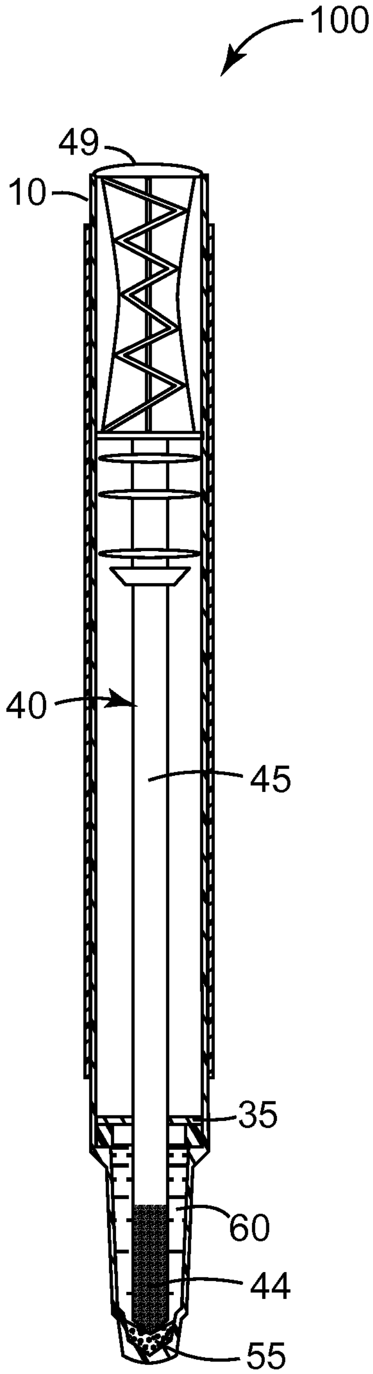
FIG. 7 is a side view, partially in section of the assembled monitoring device of FIG. 1 with the test element disposed in a second operational position with respect to the container.

The monitoring device according the present disclosure can be used by contacting the test portion of the test element with the detection reagent and the luciferin-containing substrate in the container of the monitoring device. In the illustrated embodiment of FIGS. 6-7, this comprises moving (e.g., by applying manual pressure to the handle in the direction of arrow "S") the test element 40 into a second operational position with respect to the container 10, as shown in FIG. 7. In the second operational position, the test element 40 has pierced the frangible seal 35, the luciferin-containing substrate has been pushed into contact with the first solvent 60, and the test portion 44 is contacting the first solvent 60, in which the detection reagent 56 comprising luciferase is dissolved. The first solvent 60 may be an aqueous solution with a pH that is suitable to facilitate the reaction of the detection reagent (e.g., luciferase enzyme) with luciferin and ATP. In any embodiment, contacting the test portion of the test element with the solvent in the container of the monitoring device can further comprise dissolving the optional test composition into the solvent.

Figure 8:
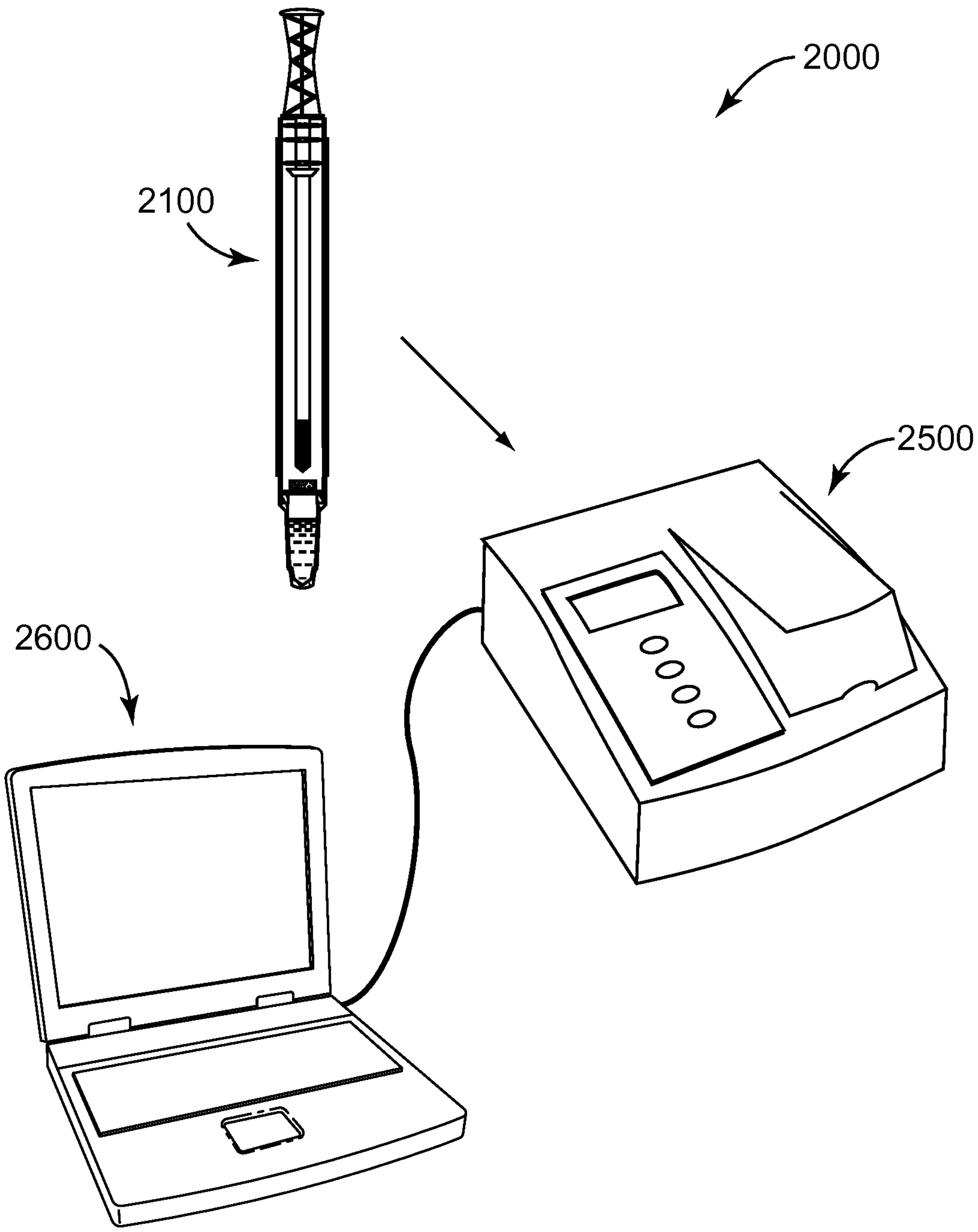
FIG. 8 is a schematic view of a system for determining enzymatic activity with a monitoring device according to the present disclosure.

FIG. 8 shows a schematic view of one embodiment of a system 2000 according to the present disclosure. The system comprises a monitoring device 2100 and an analytical instrument 2500. Optionally, the system 2000 further comprises a computer 2600.

Additional embodiments of optional components of monitoring devices and methods for using monitoring devices are as described in WO2014/058652.

In a third aspect, a method of making a luciferin-containing substrate is provided. The method includes applying to a substrate a solution containing luciferin and a solvent; and removing at least a portion of the solvent to dry the luciferin on the substrate. The luciferin-containing substrate is free of a detectable amount of reactive luciferase.

In certain embodiments, the solvent comprises water, and optionally consists essentially of luciferin and water. For instance, the luciferin-containing substrate may be free of any detectable amount of adenosine-5'-triphosphate (ATP). The solution usually contains at least 5 μg/mL luciferin, or at least 10 μg/mL luciferin, or at least 15 μg/mL luciferin, or at least 20 μg/mL luciferin, or at least 25 μg/mL luciferin.

Typically, the solution is applied to a first major surface of the substrate, such as by using a pipette to deposit a volume of the solution onto the first major surface of the substrate.

In any embodiment, the substrate is as described above with respect to the first and second aspects.

In certain embodiments, the method further comprises covering the substrate with a material opaque to visible light after applying the solution to the substrate.

In any embodiment, at least a portion of the solvent is removed using evaporation or freeze drying. Following removal of solvent, the luciferin-containing substrate preferably contains less than 10 percent by weight moisture, or less than 8 percent by weight moisture, or less than 5 percent by weight moisture, and up to 3 percent by weight moisture, or up to 3 percent by weight moisture.

In certain embodiments, the luciferin is present in the luciferin-containing substrate in an amount of at least 0.002 micrograms per substrate, or at least 0.005 micrograms per substrate, or at least 0.01 micrograms per substrate, or at least 0.05 micrograms per substrate, or at least 0.10 micrograms per substrate, or at least 0.15 micrograms per substrate, or at least 0.20 micrograms per substrate, or at least 0.30 micrograms per substrate, or up to 0.50 micrograms per substrate, or up to 0.25 micrograms per substrate; such as between 0.002 micrograms and 0.50 micrograms per substrate, or between 0.10 micrograms and 0.50 micrograms per substrate, or between 0.15 micrograms and 0.25 micrograms per substrate. The phrase "per substrate" refers to the piece of substrate, regardless of shape or size, on which the luciferin is deposited.

In any embodiment, the method further comprises disposing the luciferin-containing substrate in a package that blocks visible light, for example a package including metal foil. Optionally, the method further comprises storing the luciferin-containing substrate under controlled humidity conditions, such as at a humidity of less than 60% relative humidity, or less than 55% relative humidity, or less than 45% relative humidity, or less than 35% relative humidity, or less than 25% relative humidity, or less than 15% relative humidity, or less than 10% relative humidity. Controlled humidity conditions can be achieved in various manners, for instance using a desiccator containing a saturated salt having a known vapor pressure (e.g., lithium chloride, magnesium, chloride, magnesium nitrate, and sodium chloride). Advantageously, storing the luciferin-containing substrate at a controlled humidity levels has been found to extend the length of time the luciferin remains active (e.g., the shelf-life of the luciferin-containing substrate) as compared to storing a luciferin-containing substrate in a room having uncontrolled humidity levels.

Various embodiments are described that are luciferin-containing substrates, monitoring devices, and methods of making luciferin-containing substrates.

Embodiment 1 is a luciferin-containing substrate. The luciferin-containing substrate includes a substrate and luciferin dried on the substrate. The luciferin-containing substrate is free of a detectable amount of reactive luciferase.

Embodiment 2 is the luciferin-containing substrate of embodiment 1, wherein the substrate is selected from a nonwoven substrate, a woven substrate, a foam substrate, a polymeric film substrate, a membrane substrate, a metal foil substrate, and a microreplicated film substrate.

Embodiment 3 is the luciferin-containing substrate of embodiment 1 or embodiment 2, wherein the substrate comprises at least two polymeric materials.

Embodiment 4 is the luciferin-containing substrate of any of embodiments 1 to 3, wherein the substrate comprises cellulose, viscose, rayon, polyethylene terephthalate (PET), nylon, cotton, aluminum foil, polycarbonate (PC), polyvinylidene fluoride (PVDF), polyether sulfone (PES), polypropylene (PP), polylactic acid (PLA), or a combination thereof.

Embodiment 5 is the luciferin-containing substrate of any of embodiments 1 to 4, wherein the luciferin is present in an amount of at least 0.002 micrograms.

Embodiment 6 is the luciferin-containing substrate of any of embodiments 1 to 5, wherein the luciferin is present in an amount of at least 0.10 micrograms.

Embodiment 7 is the luciferin-containing substrate of any of embodiments 1 to 7, wherein the luciferin is present in an amount of at least 0.15 micrograms.

Embodiment 8 is the luciferin-containing substrate of any of embodiments 1 to 5, wherein the luciferin is present in an amount of between 0.002 micrograms and 0.5 micrograms.

Embodiment 9 is the luciferin-containing substrate of any of embodiments 1 to 4, wherein the luciferin is present in an amount of between 0.15 micrograms and 0.25 micrograms.

Embodiment 10 is the luciferin-containing substrate of any of embodiments 1 to 9, wherein the substrate is a nonwoven substrate.

Embodiment 11 is the luciferin-containing substrate of any of embodiments 1 to 10, wherein the substrate comprises a thickness of 10 micrometers to 500 micrometers.

Embodiment 12 is the luciferin-containing substrate of any of embodiments 1 to 11, wherein the substrate comprises a thickness of 25 micrometers to 250 micrometers.

Embodiment 13 is the luciferin-containing substrate of any of embodiments 1 to 12, wherein the luciferin-containing substrate is free of any detectable amount of adenosine-5'-triphosphate (ATP).

Embodiment 14 is the luciferin-containing substrate of any of embodiments 1 to 13, wherein the luciferin-containing substrate is disposed in a package that blocks visible light.

Embodiment 15 is the luciferin-containing substrate of embodiment 14, wherein the luciferin-containing substrate is disposed in a package including metal foil.

Embodiment 16 is the luciferin-containing substrate of any of embodiments 1 to 15, wherein less than 20% of an enzymatic activity is lost over a time of 10 weeks when stored at a temperature between 22° C. and 25° C. in the dark.

Embodiment 17 is the luciferin-containing substrate of any of embodiments 1 to 16, wherein less than 20% of an enzymatic activity is lost over a time of 4 weeks when stored at a temperature between 22° C. and 25° C. in the dark.

Embodiment 18 is the luciferin-containing substrate of any of embodiments 1 to 17, wherein less than 35% of an enzymatic activity is lost over a time of 10 weeks when stored at a temperature between 22° C. and 25° C. in the dark.

Embodiment 19 is the luciferin-containing substrate of any of embodiments 1 to 17, wherein less than 35% of an enzymatic activity is lost over a time of 4 weeks when stored at a temperature between 22° C. and 25° C. in the dark.

Embodiment 20 is the luciferin-containing substrate of any of embodiments 1 to 17, wherein less than 35% of an enzymatic activity is lost over a time of 8 weeks when stored at a temperature between 22° C. and 25° C. in the dark.

Embodiment 21 is the luciferin-containing substrate of any of embodiments 1 to 17, wherein less than 35% of an enzymatic activity is lost over a time of 4 weeks after manufacture when stored at a temperature between 37° C. and 45° C. in the dark.

Embodiment 22 is the luciferin-containing substrate of any of embodiments 1 to 21, wherein less than 10% of an enzymatic activity is lost over a time of 26 weeks when stored at a humidity of 11% and a temperature between 22° C. and 25° C. in the dark.

Embodiment 23 is the luciferin-containing substrate of any of embodiments 1 to 21, wherein less than 20% of an enzymatic activity is lost over a time of 26 weeks when stored at a humidity of 30% and a temperature between 22° C. and 25° C. in the dark.

Embodiment 24 is the luciferin-containing substrate of any of embodiments 1 to 21, wherein less than 25% of an enzymatic activity is lost over a time of 16 weeks after manufacture when stored at a humidity of 54% and a temperature between 22° C. and 25° C. in the dark.

Embodiment 25 is a monitoring device. The monitoring device includes a test element having a test portion, a detection reagent comprising luciferase, a luciferin-containing substrate, and a container having a first end with an opening and a second end opposite the first end. The container is configured to receive the test portion and configured to be operationally coupled to an analytical instrument. The detection reagent and the luciferin each are capable of participating in one or more chemical reaction that results in the formation of a detectable product.

Embodiment 26 is the monitoring device of embodiment 25, wherein the luciferin-containing substrate is free of a detectable amount of reactive luciferase.

Embodiment 27 is the monitoring device of embodiment 25 or embodiment 26, wherein the substrate is selected from a nonwoven substrate, a woven substrate, a foam substrate, a polymeric film substrate, a membrane substrate, a metal foil substrate, and a microreplicated film substrate.

Embodiment 28 is the monitoring device of any of embodiments 25 to 27, wherein the substrate comprises at least two polymeric materials.

Embodiment 29 is the monitoring device of any of embodiments 25 to 28, wherein the substrate comprises cellulose, viscose, rayon, polyethylene terephthalate (PET), nylon, cotton, aluminum foil, polycarbonate (PC), polyvinylidene fluoride (PVDF), polyether sulfone (PES), polypropylene (PP), polylactic acid (PLA), or a combination thereof.

Embodiment 30 is the monitoring device of any of embodiments 25 to 29, wherein the luciferin is present in the luciferin-containing substrate in an amount of at least 0.002 micrograms.

Embodiment 31 is the monitoring device of any of embodiments 25 to 30, wherein the luciferin is present in the luciferin-containing substrate in an amount of at least 0.10 micrograms.

Embodiment 32 is the monitoring device of any of embodiments 25 to 31, wherein the luciferin is present in the luciferin-containing substrate in an amount of at least 0.15 micrograms.

Embodiment 33 is the monitoring device of any of embodiments 25 to 30, wherein the luciferin is present in the luciferin-containing substrate in an amount of between 0.002 micrograms and 0.5 micrograms.

Embodiment 34 is the monitoring device of any of embodiments 25 to 31, wherein the luciferin is present in the luciferin-containing substrate in an amount of between 0.15 micrograms and 0.25 micrograms.

Embodiment 35 is the monitoring device of any of embodiments 25 to 34, wherein the substrate comprises a thickness of 10 micrometers to 500 micrometers.

Embodiment 36 is the monitoring device of any of embodiments 25 to 35, wherein the substrate comprises a thickness of 25 micrometers to 250 micrometers.

Embodiment 37 is the monitoring device of any of embodiments 25 to 36, wherein the monitoring device is free of any detectable amount of adenosine-5'-triphosphate (ATP).

Embodiment 38 is the monitoring device of any of embodiments 25 to 37, wherein the monitoring device is disposed in a package that blocks visible light.

Embodiment 39 is the monitoring device of embodiment 38, wherein the monitoring device is disposed in a package including metal foil.

Embodiment 40 is the monitoring device of any of embodiments 25 to 39, wherein less than 20% of an enzymatic activity is lost over a time of 10 weeks when stored at a temperature between 22° C. and 25° C. in the dark.

Embodiment 41 is the monitoring device of any of embodiments 25 to 39, wherein less than 20% of an enzymatic activity is lost over a time of 4 weeks when stored at a temperature between 22° C. and 25° C. in the dark.

Embodiment 42 is the monitoring device of any of embodiments 25 to 41, wherein less than 35% of an enzymatic activity is lost over a time of 10 weeks when stored at a temperature between 22° C. and 25° C. in the dark.

Embodiment 43 is the monitoring device of any of embodiments 25 to 42, wherein less than 35% of an enzymatic activity is lost over a time of 4 weeks when stored at a temperature between 22° C. and 25° C. in the dark.

Embodiment 44 is the monitoring device of any of embodiments 25 to 44, wherein less than 35% of an enzymatic activity is lost over a time 8 weeks when stored at a temperature between 22° C. and 25° C. in the dark.

Embodiment 45 is the monitoring device of any of embodiments 25 to 44, wherein less than 35% of an enzymatic activity is lost over a time of 4 weeks when stored at a temperature between 37° C. and 45° C. in the dark.

Embodiment 46 is the monitoring device of any of embodiments 25 to 45, wherein less than 10% of an enzymatic activity is lost over a time of 26 weeks when stored at a humidity of 11% and a temperature between 22° C. and 25° C. in the dark.

Embodiment 47 is the monitoring device of any of embodiments 25 to 45, wherein less than 20% of an enzymatic activity is lost over a time of 26 weeks when stored at a humidity of 30% and a temperature between 22° C. and 25° C. in the dark.

Embodiment 48 is the monitoring device of any of embodiments 25 to 45, wherein less than 25% of an enzymatic activity is lost over a time of 16 weeks after manufacture when stored at a humidity of 54% and a temperature between 22° C. and 25° C. in the dark.

Embodiment 49 is the monitoring device of any of embodiments 25 to 48, further comprising a test composition releasably adhered to the test portion.

Embodiment 50 is a method of making a luciferin-containing substrate. The method includes applying to a substrate a solution containing luciferin and a solvent; and removing at least a portion of the solvent to dry the luciferin on the substrate. The luciferin-containing substrate is free of a detectable amount of reactive luciferase.

Embodiment 51 is the method of embodiment 50, wherein the removing of at least a portion of the solvent comprises evaporation.

Embodiment 52 is the method of embodiment 50, wherein the removing of at least a portion of the solvent comprises freeze drying.

Embodiment 53 is the method of any of embodiments 50 to 52, wherein the solvent comprises water.

Embodiment 54 is the method of any of embodiments 50 to 53, wherein the solution is applied to a first major surface of the substrate.

Embodiment 55 is the method of any of embodiments 50 to 54, wherein the solution comprises at least 5 μg/mL luciferin.

Embodiment 56 is the method of any of embodiments 50 to 55, wherein the solution comprises at least 25 μg/mL luciferin.

Embodiment 57 is the method of any of embodiments 50 to 56, wherein the solution consists essentially of luciferin and water.

Embodiment 58 is the method of any of embodiments 50 to 57, further comprising covering the substrate with a material opaque to visible light after applying the solution to the substrate.

Embodiment 59 is the method of any of embodiments 50 to 58, wherein the luciferin-containing substrate contains less than 10 percent by weight moisture.

Embodiment 60 is the method of any of embodiments 50 to 59, wherein the luciferin-containing substrate contains less than 5 percent by weight moisture.

Embodiment 61 is the method of any of embodiments 50 to 60, wherein the luciferin-containing substrate contains up to 3 percent by weight moisture.

Embodiment 62 is the method of any of embodiments 50 to 61, wherein the substrate is selected from a nonwoven substrate, a woven substrate, a foam substrate, a polymeric film substrate, a membrane substrate, a metal foil substrate, and a microreplicated film substrate.

Embodiment 63 is the method of any of embodiments 50 to 62, wherein the substrate comprises at least two polymeric materials.

Embodiment 64 is the method of any of embodiments 50 to 63, wherein the substrate comprises cellulose, viscose, rayon, polyethylene terephthalate (PET), nylon, cotton, aluminum foil, polycarbonate (PC), polyvinylidene fluoride (PVDF), polyether sulfone (PES), polypropylene (PP), polylactic acid (PLA), or a combination thereof.

Embodiment 65 is the method of any of embodiments 50 to 64, wherein the luciferin is present in the luciferin-containing substrate in an amount of at least 0.002 micrograms.

Embodiment 66 is the method of any of embodiments 50 to 65, wherein the luciferin is present in the luciferin-containing substrate in an amount of at least 0.10 micrograms.

Embodiment 67 is the method of any of embodiments 50 to 66, wherein the luciferin is present in the luciferin-containing substrate in an amount of at least 0.15 micrograms.

Embodiment 68 is the method of any of embodiments 50 to 65, wherein the luciferin is present in the luciferin-containing substrate in an amount of between 0.002 micrograms and 0.5 micrograms.

Embodiment 69 is the method of any of embodiments 50 to 67, wherein the luciferin is present in the luciferin-containing substrate in an amount of between 0.15 micrograms and 0.25 micrograms.

Embodiment 70 is the method of any of embodiments 50 to 69, wherein the substrate is a nonwoven substrate.

Embodiment 71 is the method of any of embodiments 50 to 70, wherein the substrate comprises a thickness of 10 micrometers to 500 micrometers.

Embodiment 72 is the method of any of embodiments 50 to 72, wherein the substrate comprises a thickness of 25 micrometers to 250 micrometers.

Embodiment 73 is the method of any of embodiments 50 to 73, wherein the luciferin-containing substrate is free of any detectable amount of adenosine-5'-triphosphate (ATP).

Embodiment 74 is the method of any of embodiments 50 to 74, further comprising disposing the luciferin-containing substrate in a package that blocks visible light.

Embodiment 75 is the method of embodiment 74, wherein the package includes metal foil.

EXAMPLES

Objects and advantages of this invention are further illustrated by the following examples, but the particular materials and amounts thereof recited in these examples, as well as other conditions and details, should not be construed to unduly limit this invention. These examples are for illustrative purposes only and are not meant to be limiting on the scope of the appended claims.

Materials

Unless otherwise noted, all parts, percentages, ratios, etc., in the examples and in the remainder of the specification are by weight. Unless otherwise noted, all chemicals are available from chemical suppliers such as Sigma-Aldrich Chemical Company, St. Louis, Mo.

Example 1

Preparation of Liquid Reagent for Luminescent Activities

Luminescent light emitted from a bioluminescent reaction is measured in a liquid reagent. The final liquid reagent composition at the time of testing comprises an ADA buffer, luciferase enzyme at a concentration of 9 μg/mL, and a luciferin substrate at 0.4 μg/mL (Table 1). The ADA buffer used in this experiment was stored at 4° C., while luciferase and luciferin stock solutions are always kept at −20° C. before use. The composition of the ADA buffer pH 6.4-6.6 is listed in Table 1, below. A solution of 735 μg/mL Luciferase enzyme was prepared by a 10× dilution in ADA buffer, aliquots stored at −20° C. The 40 μg/mL Luciferin substrate: luciferin powder in Milli Q water, aliquots, were stored at −20° C. The 0.1 μg/mL ATP testing sample: ATP powder in Milli Q water, aliquots, were stored at −20° C.

TABLE 1

| Liquid reagent composition | | |
|---|---|---|
| Component | Amount grams/liter | Source |
| ADA BUFFER pH 6.4-6.6 | | |
| Water (Milli Q) | QS fill to 1 liter | EMD Millipore Corp. (Billerica, MA) |
| ADA Free Acid [CAS No. 26239-55-4] | 0.308 | Sigma-Aldrich Co. (St. Louis, MO) |
| ADA Disodium Salt [CAS No. 41689-31-0] | 3.366 | Sigma-Aldrich Co. (St. Louis, MO) |

TABLE 1-continued

| Liquid reagent composition | | |
|---|---|---|
| Component | Amount grams/liter | Source |
| EDTA Disodium Salt Dihydrate [CAS No. 6381-92-6] | 0.707 | Sigma-Aldrich Co. (St. Louis, MO) |
| Magnesium Acetate Tetrahydrate [CAS No. 16674-78-5] | 2.037 | Sigma-Aldrich Co. (St. Louis, MO) |
| Sodium Azide [CAS No. 26628-22-8] | 0.5 | Sigma-Aldrich Co. (St. Louis, MO) |
| D-Sorbitol [CAS No. 50-70-4] | 237.5 | Molekula LTD (Gillingham, UK) |
| Bovine Serum Albumin [CAS No. 9048-46-8] | 0.5 | Sigma-Aldrich Co. (St. Louis, MO) |
| UltraGlo Luciferase (Type E140X) | 0.0009% (9 mg/L) | Promega Corp. (Madison, WI) |
| Luciferin (Type XE160X) | 0.00003-0.00004% (0.3-0.4 mg/L) | Promega Corp. (Madison, WI) |

Example 2

Measurement of Luminescent Activities Procedure

The amount of luciferin at a concentration of 0.4 μg/mL in a liquid reagent is sufficient to facilitate a light-emitting reaction in the presence of luciferase and ATP. Liquid ATP at a predefined concentration was used as the source of ATP in the following examples.

Measurement of Luminescent Activity Experimental Procedure:

1. Added 400 μL of ADA buffer (TABLE 1) into a clean measurement cuvette.
2. Added 4.9 μL of 735 μg/mL luciferase stock solution (10× dilution in ADA buffer) and gently mixed.
3. Placed one of the sample disks spiked with luciferin into the cuvette allowing it to mix with the solution in the cuvette.
4. For the liquid luciferin control samples, pipetted 4 μL of each of the aged liquid samples into the same testing reagent as that used for the sample nonwoven disks, or other example substrates.
5. Pipetted 5 μL of 0.1 μg/mL of ATP (available from Sigma-Aldrich Co., St. Louis, Mo.) into each cuvette to start the luminescent reaction.
6. After ATP was added to each cuvette, counted for 30-60 seconds, and gently shook the cuvette while counting.
7. Placed the cuvette into the handheld 3M CLEAN-TRACE NG Luminometer (available from 3M Company of St. Paul, Minn., USA) to read the RLU (Relative Light Units: the amount of light produced during the reaction).

Comparative Example 1

Luciferin, as the luminescent substrate, is apt to degrade in solution during storage thus limiting the luminescent reaction. An experiment was conducted with luciferase and luciferin each aged separately and compared to a reagent mixture of luciferase and luciferin aged together. All prepared samples were covered with aluminum foil to protect from photo-degradation during aging. The Product Control was a 3M CLEAN-TRACE WATER—TOTAL ATP product (available from 3M Company of St. Paul, Minn., USA) stored at 4° C. Samples stored at 4° C. were used as the controls in that they were expected to show minimal degradation compared to samples stored at temperatures of 25° C. (room temperature) and 37° C. (oven). Aged luciferase samples included fresh luciferin being added to the aged solution right before ATP testing. Aged luciferin samples included fresh luciferase being added to the aged solution right before ATP testing. The results of this comparative example show that adding fresh luciferin to the aged luciferase-containing reagent reveals superior luminescent stability compared to aging luciferase and luciferin in a mixture.

TABLE 2

| COMPARATIVE EXAMPLE 1 | | | | | | | | |
|---|---|---|---|---|---|---|---|---|
| | Measured Luminescent Activity (RLU) | | | | | | | |
| | 34 weeks of storage | | | | 51 weeks of storage | | | |
| Comparative Samples | Product Control | 4° C. | 25° C. | 37° C. | Product Control | 4° C. | 25° C. | 37° C. |
| Aged luciferin + luciferase solution | 63767 | 66957 | 44693 | 7491 | 64632 | 63241 | 34110 | 3508 |
| Aged luciferase + fresh luciferin | — | 79020 | 83431 | 27212 | — | 87518 | 94085 | 21053 |

TABLE 2-continued

| COMPARATIVE EXAMPLE 1 | | | | | | | | |
|---|---|---|---|---|---|---|---|---|
| | Measured Luminescent Activity (RLU) | | | | | | | |
| | 34 weeks of storage | | | | 51 weeks of storage | | | |
| Comparative Samples | Product Control | 4° C. | 25° C. | 37° C. | Product Control | 4° C. | 25° C. | 37° C. |
| Aged luciferin + fresh luciferase | — | 86875 | 58504 | 15065 | — | 60539 | 36567 | 10178 |

Example 3

Preparation of Dried Luciferin on Nonwoven Substrates

Samples of luciferin were dried on the various nonwoven substrates that are listed in TABLE 3, according to the following procedure. A 7 mm disk (circle) of each nonwoven sheet material was punched out. Each individual disk was overlaid on a separate well of a standard 96 well plate, without touching the bottom of the well. Powdered luciferin was dissolved into sterilized (autoclaved and cooled) MilliQ water to a final concentration at 40 μg/mL. An amount of 4 μL of the 40 μg/mL the luciferin solution was pipetted onto each 7 mm diameter nonwoven disks of the material described above. The 96 well plate was loosely covered with aluminum foil to protect the luciferin spiked nonwoven disks from light to prevent photo-degradation of the luciferin. The nonwoven disks were allowed to dry for about 3-4 hours at room temperature. After drying, luciferin spiked nonwoven disks were transferred into a 1.5 mL Eppendorf tube (approximately 7-8 disks/tube of the same type of nonwoven) and the Eppendorf tube was covered with aluminum foil to prevent light exposure.

Example 4

Aging of Dried Luciferin on Nonwoven Substrates

The Eppendorf tubes with the luciferin spiked nonwoven disks described in Example 3 were stored at 4° C. (refrigerator), room temperature (25° C.), 37° C. oven, and 45° C. oven, to assess the stability over time of the luciferin dried on the various nonwoven substrates. A 500 μL microtube containing 50 μL of 40 μg/mL liquid luciferin solution was stored together with nonwoven disks at each aging temperature for comparison testing. When the nonwoven disk containing dried luciferin was mixed into the luciferase containing solution, luciferin was rehydrated immediately from nonwoven, allowing the luciferase to react with the ATP added into each sample cuvette. The reaction was allowed to equilibrate, typically about 30-60 seconds, and then measured with the handheld 3M CLEAN-TRACE NG Luminometer. Luminescent activity measured from samples stored at 4° C. were used as the control to compare with other samples aged at the higher temperatures. The nonwoven disks containing dried luciferin were kept dry and separate from the testing reagent during storage. The stability of dried luciferin was determined by measuring the luminescent activity every 2-4 weeks for up to 32 weeks.

TABLE 3

| NONWOVEN SUBSTRATES | | | | |
|---|---|---|---|---|
| Nonwoven ID | Materials | Nonwoven Processed Format | Basis Weight (gsm) | Manufacturer |
| B9260 | PET | Carded/powder bond | 60 | HDK Industries, Rogersville, TN, USA |
| HEF-140-114 | Rayon | Spunlace | 81 | Suominen Nonwovens, Helsinki, Finland |
| SX-500 | 70 Tencel/30 PET | Spunlace | 60 | Suominen Nonwovens, Helsinki, Finland |
| UNIFIL 125 | PET/Rayon | Drylaid/Resin bond | 42 | Midwest Filtration LLC, Cincinnati, OH, USA |
| WC 110 | 50 PET/50 Viscose | Carded/Needle punched | 110 | NonWoven Solutions LLC, Ingleside, IL, USA |

The RLU results for weeks 0, 8, 14, 18, 26, 32, 52, and 78 are shown in Tables 4A-4D, below. The amount of luminescent light produced (expressed in relative light units (RLU)) by the reaction was correlated to the stability of the luciferin dried on the nonwoven substrate. The Liquid Control was 4 μL of 40 μg/mL luciferin liquid solution aged along with the luciferin spiked and dried nonwoven disks. The Product Control was 3M CLEAN-TRACE WATER—TOTAL ATP product stored at 4° C.

TABLE 4A

STABILITY OF LUCIFERIN ON NONWOVEN SUBSTRATES

| Nonwoven substrate with dried luciferin | Measured Luminescent Activity (RLU) Week 0 4° C. | Week 8 4° C. | Week 8 25° C. | Week 8 37° C. | Week 8 45° C. | Week 14 4° C. | Week 14 25° C. | Week 14 37° C. | Week 14 45° C. |
|---|---|---|---|---|---|---|---|---|---|
| B9260 | 45083 | 35124 | 20176 | 2986 | 1513 | 12530 | 12213 | 1749 | 605 |
| HEF-140-114 | 63550 | 81364 | 65388 | 48871 | 46071 | 40543 | 48577 | 36652 | 27100 |
| SX-500 | 56313 | 79640 | 67210 | 59198 | 50253 | 47063 | 44197 | 39444 | 34336 |
| UNIFIL 125 | 51205 | 78276 | 64539 | 49655 | 41742 | 34784 | 29595 | 31664 | 21024 |
| WC-100 | 56803 | 73746 | 68817 | 69596 | 42613 | 42188 | 24599 | 39071 | 28947 |
| Liquid Control | 65182 | 88581 | 69149 | 42951 | 10333 | 66289 | 52248 | 25397 | 5014 |
| Product Control | — | — | — | — | — | 55194 | — | — | — |

TABLE 4B

STABILITY OF LUCIFERIN ON NONWOVEN SUBSTRATES

| Nonwoven substrate with dried luciferin | Measured Luminescent Activity (RLU) Week 0 4° C. | Week 18 4° C. | Week 18 25° C. | Week 18 37° C. | Week 18 45° C. | Week 26 4° C. | Week 26 25° C. | Week 26 37° C. | Week 26 45° C. |
|---|---|---|---|---|---|---|---|---|---|
| B9260 | 45083 | 11176 | 10846 | 1581 | 388 | 35124 | 20176 | 2986 | 1513 |
| HEF-140-114 | 63550 | 75036 | 48007 | 44262 | 26895 | 81364 | 65388 | 48871 | 46071 |
| SX-500 | 56313 | 71436 | 56226 | 43721 | 34579 | 79640 | 67210 | 59198 | 50253 |
| UNIFIL 125 | 51205 | 57089 | 45751 | 32971 | 22757 | 78276 | 64539 | 49655 | 41742 |
| WC-100 | 56803 | 53291 | 50026 | 49440 | 27633 | 73746 | 68817 | 69596 | 42613 |
| Liquid Control | 65182 | 72706 | 55358 | 14599 | 2504 | 88581 | 69149 | 42951 | 10333 |
| Product Control | — | 63767 | — | — | — | — | — | — | — |

TABLE 4C

STABILITY OF LUCIFERIN ON NONWOVEN SUBSTRATES

| Nonwoven substrate with dried luciferin | Measured Luminescent Activity (RLU) Week 0 4° C. | Week 32 4° C. | Week 32 25° C. | Week 32 37° C. | Week 32 45° C. |
|---|---|---|---|---|---|
| B9260 | 45083 | 12530 | 12213 | 1749 | 605 |
| HEF-140-114 | 63550 | 40543 | 48577 | 36652 | 27100 |
| SX-500 | 56313 | 47063 | 44197 | 39444 | 34336 |
| UNIFIL 125 | 51205 | 34784 | 29595 | 31664 | 21024 |
| WC-100 | 56803 | 42188 | 24599 | 39071 | 28947 |
| Liquid Control | 65182 | 66289 | 52248 | 25397 | 5014 |
| Product Control | — | 55194 | — | — | — |

TABLE 4D

| STABILITY OF LUCIFERIN ON NONWOVEN SUBSTRATES | | | | | | | | | |
|---|---|---|---|---|---|---|---|---|---|
| Nonwoven | Measured Luminescent Activity (RLU) | | | | | | | | |
| substrate with dried luciferin | Week 0 4° C. | Week 52 4° C. | 25° C. | 37° C. | 45° C. | Week 78 4° C. | 25° C. | 37° C. | 45° C. |
| B9260 | 45083 | 9405 | 3958 | 578 | 680 | 5383 | 941 | 592 | 341 |
| HEF-140-114 | 63550 | 35287 | 25438 | 21541 | 20411 | 31017 | 13551 | 12404 | 11343 |
| SX-500 | 56313 | 47194 | 35489 | 29155 | 26610 | 34698 | 23441 | 21632 | 19972 |
| UNIFIL 125 | 51205 | 27912 | 17157 | 21267 | 17564 | 15069 | 13167 | 13412 | 10030 |
| WC-100 | 56803 | 38839 | 33443 | 22638 | 23889 | 24797 | 18750 | 14550 | 13088 |
| Liquid Control | 65182 | 52898 | 25740 | 265 | 6 | 40652 | 18092 | | |
| Product Control | — | 63042 | — | — | — | — | — | — | — |

Example 5

Dried Luciferin on Various Substrates

An amount of 4 μL of the 40 μg/mL luciferin liquid solution was pipetted and dried at room temperature for 3 days onto 7 mm disks punched (cut) from various substrates described in TABLE 5. Luminescent activity was tested in the same manner as described in Example 4.

TABLE 5

| LUMINESCENT ACTIVITY OF LUCIFERIN DRIED ON VARIOUS SUBSTRATES | | | | | |
|---|---|---|---|---|---|
| Substrate Format | Material - Hydrophilicity | Description | Source | RLU | RLU Std. Dev. |
| Film | PVA hydrophilic | POVAL PVA 235 (Polyvinyl alcohol) | Kuraray America, Inc. | 14065 | 1793 |
| Film | PET hydrophobic | MELINEX 618 50 μm (2 mil) thick polyethylene terephthalate | E.I. du Pont de Nemours and Co,, Wilmington, DE, USA | 75628 | 7664 |
| Film | Polycarbonate hydrophobic | LEXAN 8010 175 μm (7 mil) thick polycarbonate film | GE advanced Materials, Pittsfield, MA | 67051 | 3325 |
| Textured film | LDPE hydrophobic | M1* Microreplicated low density polyethylene film with primary and secondary channels | 3M Company, St. Paul, MN, USA | 55638 | 8673 |
| Textured film | LDPE (surface treated) hydrophilic | M2* Microreplicated low density polyethylene film with primary and secondary channels with a hydrophilic treatment | 3M Company, St. Paul, MN, USA | 70569 | 2331 |
| Woven | Polyester knit hydrophilic | Berkshire, 100% Super PoLX 1200 | Berkshire Corporation, Great Barrington, MA, USA | 25206 | 4154 |
| Woven | Cotton Wipe hydrophilic | ITW Company, 100%, TX 304, Tex wipe | Texwipe, Kernersville, NC, USA | 23906 | 2389 |
| Membrane | Nylon hydrophilic/ hydrophobic | Zetapor Membrane STL01, Part Number: P1100-STL01 | 3M Purification, Inc., Meriden CT, USA | 5241 | 1564 |
| Membrane | BK080 hydrophilic/ hydrophobic | Zetapor Membrane BLA010, Part Number: P1200-BLA010 | 3M Purification, Inc., Meriden CT, USA | 6558 | 1208 |

TABLE 5-continued

LUMINESCENT ACTIVITY OF LUCIFERIN DRIED ON VARIOUS SUBSTRATES

| Substrate Format | Material - Hydrophilicity | Description | Source | RLU | RLU Std. Dev. |
|---|---|---|---|---|---|
| Membrane | PVDF Hydrophilic GVWP/ Hydrophobic GVHP | Millipore, 0.221 µm GV (WP philic, HP phobic) | EMD Millipore, a division of Merck KGaA, Darmstadt, Germany | 67935 | 3560 |
| Membrane | PES (Polyether-sulfone) membrane hydrophilic | MicroPES ® 2F PH, 0.2 µm | Membrana GmbH, Charlotte, NC, USA | 56373 | 2368 |
| Membrane | PP membrane hydrophobic | Pall GHP, 0.22 µm | Pall Corporation, Port Washington, NY, USA | 59749 | 335 |
| Nonwoven | Hydroguard hydrophilic | Haynes, PET/Cellulose/50.9 gsm | Haynes Companies, Inc., Indianapolis, IN, USA | 19730 | 2744 |
| Nonwoven | Sontara 8005 hydrophobic | Dupont, PET/63.5 gsm | E.I. du Pont de Nemours and Co., Wilmington, DE, USA | 63157 | 1065 |
| Nonwoven | PLA nonwoven hydrophilic | Changlong, Polylactic acid/40 gsm | Wenzhou Changlong Textile Technology, Zhejiang, China | 64350 | 9639 |
| Nonwoven | PE85-20 hydrophobic | Bostik, Copolyester/20 gsm | Bostik, Wauwatosa, WI | 62407 | 1681 |
| Nonwoven | SX 500 hydrophilic | Suominen Nonwovens, 70 Tencel/30 PET | Suominen Nonwovens, Helsinki, Finland | 59980 | 4237 |
| Nonwoven | WC 110 hydrophilic | Nonwoven Solutions, 50 PET/50 Viscose | NonWoven Solutions LLC, Ingleside, IL, USA | 64463 | 1743 |
| Paper | Hardened Paper hydrophilic | Whatman hardened low ash grade filter paper, Cat. No. 1454-110 | GE Healthcare Bio-Sciences Corp., Piscataway, NJ, USA | 46773 | 5094 |
| Paper | Quantitative Paper hydrophilic | Whatman quantitative filter paper, Cat. No. 1004-110 | GE Healthcare Bio-Sciences Corp., Piscataway, NJ, USA | 47092 | 8491 |
| Paper | Paper Towel Paper hydrophilic | WYPALL wipers | Kimberly-Clark Professional Roswell, GA, USA | 61348 | 1792 |
| Metal film | Aluminum Hydrophobic | Reynolds Wrap Standard Foil | Reynolds Consumer Products, Lake Forrest IL, USA | 59860 | 1640 |

TABLE 5-continued

| LUMINESCENT ACTIVITY OF LUCIFERIN DRIED ON VARIOUS SUBSTRATES | | | | | |
|---|---|---|---|---|---|
| Substrate Format | Material - Hydrophilicity | Description | Source | RLU | RLU Std. Dev. |
| | Liquid Control | 4 μL of 40 μg/mL luciferin in liquid form | — | 77180 | 1030 |
| | Product Control | 3M CLEAN-TRACE WATER - TOTAL ATP | 3M Company, St. Paul, MN, USA | 66923 | 183 |

*M1 & M2 Microreplicated low density polyethylene films with primary and secondary channels are describe in co-pending US Provisional patent application number 61/983,585, in the first paragraph of the example section. M2 is the same as M1 except that M2 has hydrophilic coating applied to the film which has silane and siloxane groups.

Example 6

Dried Luciferin on Nonwovens

Comparative Example 2

Dried Luciferase & Dried Mixtures of Luciferin and Luciferase on Nonwovens

For the "dried luciferin" samples, an amount of 4 μL of the 40 μg/mL luciferin liquid solution was pipetted onto 7 mm disks of the nonwoven substrates listed in TABLE 6 and dried at room temperature for 3 days prior to analysis (equivalent to 0.4 μg/mL, in the 3M CLEAN-TRACE WATER—TOTAL ATP product). For the "dried luciferase" samples, 4.9 μL of 735 μg/mL luciferase buffer solution was pipetted onto 7 mm disks of the nonwoven substrates listed in TABLE 6 and dried at room temperature for 3 days prior to analysis (equivalent to 9 μg/mL in the 3M CLEAN-TRACE WATER—TOTAL ATP product). Samples of a mixture of luciferase and luciferin (4.9 μL of 735 μg/mL luciferase buffer solution and 4 μL of 40 μg/mL luciferin solution) were pipetted onto 7 mm disks of the nonwoven substrates listed in TABLE 6 and dried at room temperature for 3 days prior to analysis. The Control was freshly prepared ADA buffer solution containing 0.4 μg/mL luciferin and 9 μg/mL luciferase. Luminescent activities were tested in the same manner as described in EXAMPLE 4.

TABLE 6

| LUMINESCENT ACTIVITY OF DRIED LUCIFERASE, DRIED LUCIFERIN, DRIED MIXTURES OF LUCIFERIN AND LUCIFERASE | | | |
|---|---|---|---|
| | Measured Luminescent Activity (RLU) | | |
| Nonwoven ID | Dried luciferin | Dried luciferase | Dried luciferase + luciferin |
| B9260 | 49902 | 29137 | 36444 |
| HEF-140-114 | 59955 | 46101 | 37521 |
| SX-500 | 53253 | 52531 | 43274 |
| UNIFIL 125 | 48188 | 61224 | 42503 |
| WC 110 | 56989 | 57954 | 50274 |
| Control | 65243 | — | — |

Example 7

Dried Luciferin on Nonwovens

Luminescent activities were tested in the same manner as described in Example 4, to compare differences in storage humidity.

Experimental Procedure:

1. Punched a 7 mm disk from a selected nonwoven sheet listed in TABLE 7.
2. Using a 96 well plate, each individual disk was overlaid on each well without touching the bottom of the well.
3. Dissolved luciferin powder into autoclaved MilliQ water to a final concentration of 40 μg/ml.
4. Pipetted 4 μl of luciferin solution on each 7 mm diameter nonwoven disk.
5. Loosely covered the nonwoven disk with aluminum foil to protect it from light.
6. Allowed the nonwoven disk to dry for about 3-4 hours at room temperature.
7. After drying, transferred the nonwoven disks into a 5 ml micro tube and cover with aluminum foil to prevent light exposure.
8. Stored the micro tube with nonwoven disks at 4° C., room environment, and humidity controlled desiccator at room temperature,
9. A 1-ml Eppendorf tube containing 500 μl of liquid luciferin solution was stored together with nonwoven disks at each aging condition.
10. Nonwoven disks stored at 4° C. was used as the control to compare with the results from other samples.

TABLE 7

| NONWOVEN SUBSTRATES | | | | |
|---|---|---|---|---|
| Nonwoven ID | Materials | Nonwoven Processed Format | Basis Weight (gsm) | Manufacturer |
| SX-500 | 70 Tencel/30 PET | Spunlace | 60 | Suominen Nonwovens, Helsinki, Finland |
| WC 70 | 50 PET/50 Viscose | Carded/Needle punched | 70 | NonWoven Solutions LLC, Ingleside, IL, USA |
| WC 110 | 50 PET/50 Viscose | Carded/Needle punched | 110 | NonWoven Solutions LLC, Ingleside, IL, USA |

Example 8

Aging of Dried Luciferin on Nonwovens

Aging conditions for dried luciferin samples:

4° C.: Samples kept in refrigerator and were considered as control samples.

Room: Samples kept in air-conditioning controlled room environment.

Desiccator: Samples kept in a humidity-controlled dry desiccator at room temperature.

Four desiccators with different humidity levels were used to store the dried luciferin containing nonwoven disks at room temperature. The saturated salt solutions, made up as a slushy mixture with distilled water and a chemically pure salt, was enclosed in the sealed desiccator to maintain the humidity at a designed level. A humidity meter was placed inside of desiccator to monitor the humidity during storage.

Relative humidity conditions for sample aging:

4° C.: Samples were stored in the refrigerator and considered as controls (e.g., fresh).

11%: Placed saturated Lithium Chloride salt in the desiccator to control the relative humidity.

29%: Placed saturated Magnesium Chloride in the desiccator to control the relative humidity.

54%: Placed saturated Magnesium Nitrate in the desiccator to control the relative humidity.

74%: Placed saturated Sodium Chloride in the desiccator to control the relative humidity.

Example 9

Measurement of Luminescent Activities

The amount of luciferin at a concentration of 0.4 μg/ml in a liquid reagent was sufficient to facilitate a light-emitting reaction in the presence of luciferase and ATP. Liquid ATP at a predefined concentration was used as the source of ATP in the present disclosure. The experimental procedure was as described above in Example 2.

Comparative Example 2

Separated Luciferin from Solutions Containing Luciferase During Storage

As noted above in Comparative Example 1, luciferin, as the luminescent substrate, is apt to be oxidized in the solution during storage to form an oxyluciferin which is considered an enzyme inhibitor in the luminescent reaction. Thus, an experiment was conducted with luciferase and luciferin aged separately in comparison to the result, which uses the mixed luciferase and luciferin reagent during aging.

TABLE 8

LUMINESCENT ACTIVITY AFTER AGING AT DIFFERENT CONDITIONS

| Aging | Measured Luminescent Activity (RLU) | | | | | | | |
|---|---|---|---|---|---|---|---|---|
| | 28 Weeks | | | | 52 Weeks | | | |
| Conditions | SX 500 | WC70 | WC110 | Liquid | SX 500 | WC70 | WC110 | Liquid |
| 4C | 53694 | 51308 | 61210 | 64752 | 73842 ± 3058 | 64236 ± 2940 | 74495 ± 2686 | 90271 ± 1005 |
| Room | 42236 | 38653 | 42051 | 50325 | 52398 ± 4837 | 44192 ± 1432 | 45705 ± 1447 | 60403 ± 2121 |
| Desiccator | 52939 | 53658 | 64681 | | 71127 ± 3889 | 75028 ± 1558 | 75693 ± 02579 | |

Sample description (All samples were covered with aluminum foil to protect from light)

4° C.: Samples stored at 4° C., used as the control to compare to room storage conditions.

Room: Samples stored at room temperature without humidity control.

Desiccator: Samples stored in a humidity controlled desiccator at room temperature.

SX500, WC70, and WC110 were different nonwovens containing dried luciferin (TABLE 7).

Liquid: 4 μl of 40 μg/ml luciferin liquid solution as loaded and aged on nonwoven disks, used to compare with the nonwoven samples.

52 weeks result is the average of triplicate results.

The samples stored at 4° C. were the control to compare those aged at room and desiccator conditions. After 1 year (i.e., 52 weeks) of aging, luminescent activity in the samples aged at desiccator conditions remained the same as that of the 4° C. control, while the samples at room temperature without humidity control showed more than 30% loss in activity.

Example 10

Humidity Effects on Luciferin Stability During Storage

It has been discovered that even the humidity at room temperature also causes the deterioration of dried luciferin on nonwoven, resulting the decrease in luminescent activity. In order to understand in which degree the humidity may affect the stabilization of luciferin, four desiccators with different humidity were used to store the dried luciferin containing nonwoven disks at room temperature. SX500 and WC110 were two different nonwovens containing dried luciferin (TABLE 9). Samples were stored as in Example 8.

In comparison to the samples stored at 4° C., dried luciferin on nonwovens was stable at 11% humidity as no activity loss was observed after 26 weeks of aging. About 10%, 20%, and 40% in luminescent activity loss was observed for luciferin samples stored at 29%, 54%, and 74% relative humidity, respectively. TABLE 10 provides a normalization of the luminescent activities reported in TABLE 9, normalized to the 4° C. control.

TABLE 9

| LUMINESCENT ACTIVITY (RLU) AFTER AGING AT DIFFERENT HUMIDITIES | | | | | | | |
|---|---|---|---|---|---|---|---|
| | | Aging Time (Weeks) | | | | | |
| Non-woven | Humidity | 4 | 8 | 12 | 16 | 21 | 26 |
| SX 500 | 4° C. | 66191 | 57455 | 55792 | 52295 | 53429 | 54227 |
| | 11% | 66132 | 56910 | 52938 | 54513 | 53160 | 56329 |
| | 29% | 64020 | 53993 | 53612 | 51578 | 46353 | 48754 |
| | 54% | 59036 | 52616 | 47591 | 47002 | 44941 | 42895 |
| | 74% | 58028 | 45539 | 41793 | 37539 | 35630 | 32467 |
| WC 110 | 4° C. | 70057 | 56910 | 54197 | 53584 | 52517 | 52858 |
| | 11% | 70057 | 56894 | 53618 | 53266 | 51423 | 50563 |
| | 29% | 66381 | 52125 | 51705 | 49443 | 47519 | 45232 |
| | 54% | 65070 | 50572 | 48028 | 43953 | 40630 | 41244 |
| | 74% | 63394 | 46668 | 42764 | 39709 | 33161 | 31817 |

TABLE 10

| NORMALIZED LUMINESCENT ACTIVITY FROM TABLE 9 AS RELATIVE RLU | | | | | | | |
|---|---|---|---|---|---|---|---|
| Non- | | Aging Time (Weeks) | | | | | |
| woven | Humidity | 4 | 8 | 12 | 16 | 21 | 26 |
| 5X 500 | 4° C. | 1 | 1 | 1 | 1 | 1 | 1 |
| | 11% | 0.9991 | 0.9905 | 0.9489 | 1.0424 | 0.9950 | 1.0388 |
| | 29% | 0.9672 | 0.9397 | 0.9609 | 0.9863 | 0.8676 | 0.8991 |
| | 54% | 0.8919 | 0.9158 | 0.8530 | 0.8988 | 0.8411 | 0.7910 |
| | 74% | 0.8767 | 0.7926 | 0.7491 | 0.7178 | 0.6669 | 0.5987 |
| WC 110 | 4° C. | 1 | 1 | 1 | 1 | 1 | 1 |
| | 11% | 0.9949 | 0.9997 | 0.9893 | 0.9941 | 0.9792 | 0.9566 |
| | 29% | 0.9475 | 0.9159 | 0.9540 | 0.9227 | 0.9048 | 0.8557 |
| | 54% | 0.9288 | 0.8886 | 0.8862 | 0.8203 | 0.7737 | 0.7803 |
| | 74% | 0.9049 | 0.8200 | 0.7891 | 0.7411 | 0.6314 | 0.6019 |

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A luciferin-containing substrate comprising a substrate and luciferin dried on the substrate, wherein the luciferin-containing substrate is free of a detectable amount of reactive luciferase, wherein the substrate is selected from a nonwoven fibrous substrate layer, a woven substrate layer, a polymeric foam substrate, a polymeric film substrate, and a microreplicated film, and wherein the luciferin is present in an amount of between 0.002 micrograms and 0.5 micrograms.

2. The luciferin-containing substrate of claim 1, wherein the substrate is selected from a nonwoven fibrous substrate layer, a woven substrate layer, a polymeric film substrate, and a microreplicated film.

3. The luciferin-containing substrate of claim 1, wherein the luciferin is present in an amount of between 0.10 micrograms and 0.5 micrograms.

4. The luciferin-containing substrate of claim 1, wherein the substrate is a nonwoven fibrous substrate layer.

5. The luciferin-containing substrate of claim 1, wherein the luciferin-containing substrate is disposed in a package that blocks visible light.

6. The luciferin-containing substrate of claim 1, wherein less than 20% of a luminescent activity is lost over a time of 4 weeks when stored at a temperature between 22° C. and 25° C. in the dark.

7. The luciferin-containing substrate of claim 1, wherein less than 10% of a luminescent activity is lost over a time of 26 weeks when stored at a humidity of 11% and a temperature between 22° C. and 25° C. in the dark.

8. The luciferin-containing substrate of claim 1, wherein the substrate comprises a thickness of 10 micrometers to 500 micrometers.

* * * * *